US008633250B2

(12) United States Patent
Schnellmann et al.

(10) Patent No.: US 8,633,250 B2
(45) Date of Patent: Jan. 21, 2014

(54) CELL REPAIR AND REGENERATION BY SURAMIN AND RELATED POLYSULFONATED NAPTHYLUREAS

(75) Inventors: Rick G. Schnellmann, Mt. Pleasant, SC (US); Shougang Zhuang, Cheshire, CT (US)

(73) Assignee: MUSC Foundation for Research Development, Charleston, SC (US)

( * ) Notice: Subject to any disclaimer, the term of this patent is extended or adjusted under 35 U.S.C. 154(b) by 411 days.

(21) Appl. No.: 11/622,285

(22) Filed: Jan. 11, 2007

(65) Prior Publication Data
US 2007/0203234 A1 Aug. 30, 2007

Related U.S. Application Data

(60) Provisional application No. 60/759,118, filed on Jan. 12, 2006.

(51) Int. Cl.
*A61K 31/17* (2006.01)
*A61K 31/138* (2006.01)

(52) U.S. Cl.
USPC .......................................... 514/577; 514/576

(58) Field of Classification Search
None
See application file for complete search history.

(56) References Cited

U.S. PATENT DOCUMENTS 5,173,509 A 12/1992 Walther et al.

FOREIGN PATENT DOCUMENTS

EP 0486809 A2 * 5/1992 ........... A61K 31/185

OTHER PUBLICATIONS

Pascher et al.; "Biologics in the treatment of transplant rejection and ischemia/reperfusion injury: new applications for TNFalpha inhibitors?"; 2005; ; BioDrugs; 19(4): 211-31.*
Zager et al.; "Ischemic proximal tubular injury primes mice to endotoxin-induced TNF-α generation and systemic release"; Mar. 29, 2005; A. J. Physiol. Renal. Physiol.; 298: F289-F297.*
Wiviott et al.; "Unstable Angina and Non-ST-Segment Elevation Myocardial Infarction: Part I. Initial Evaluation and Management and Hospital Care"; 2004; American Family Physician 70(3): 525-532.*
Weber; "Monitoring Tissue Repair and Fibrosis From a Distance"; 1997; Circulation; 96(8): 2488-2492, pp. 1-11.*
Chandrashekhar; "Role of apoptosis in ventricular remodeling"; 2005; Curr, Heart Fail Rep. 2(1): 18-22.*
Donnahoo et al.; "Review Article: The Role of Tumor Necrosis Factor in Renal Ischemia-Reperfusion Injury"; 1999; The Journal of Urology; 162: 196-203.*
Meldrum et al.; Review: Role of TNF in Mediating Renal Insufficiency Following Cardiac Surgery: Evidence of a Postbypass Cardiorenal Syndrome; 1999; Journal of Surgical Research; 85: 185-199.*
Anderson RJ and Ray CJ (1998) Potential autocrine and paracrine mechanisms of recovery from mechanical injury of renal tubular epithelial cells. Am J Physiol 274:F463-472.
Atfi A, Drobetsky E, Boissonneault M, Chapdelaine a and Chevalier S (1994) Transforming growth factor beta down-regulates Src family protein tyrosine kinase signaling pathways. J Biol Chem 269:30688-30693.
Barrett MP, Burchmore RJ, Stich A, Lazzari JO, Frasch AC, Cazzulo JJ and Krishna S (2003) The trypanosomiases. Lancet 362:1469-1480.

(Continued)

*Primary Examiner* — Timothy Thomas
(74) *Attorney, Agent, or Firm* — Parker Highlander PLLC

(57) ABSTRACT

Disclosed herein are compositions and methods for promoting the repair and regeneration of injured tissues, such as injuries resulting from ischemic damage.

8 Claims, 14 Drawing Sheets

(56) References Cited

OTHER PUBLICATIONS

Betsholtz C, Johnsson A, Heldin CH and Westermark B (1986) Efficient reversion of simian sarcoma virus-transformation and inhibition of growth factor-induced mitogenesis by suramin. Proc Natl Acad Sci U S A 83:6440-6444.

Boland S, Boisvieux-Ulrich E, Houcine O, Baeza-Squiban A, Pouchelet M, Schoevaert D and Marano F (1996) TGF beta 1 promotes actin cytoskeleton reorganization and migratory phenotype in epithelial tracheal cells in primary culture. J Cell Sci 109:2207-2219.

Braddock, PS., Hu DE, Fan, TP., Stratford, IJ., Harris, AL., and Bicknell, R. (1994). A structure-activity analysis of antagonism of the growth factor and angiogenic activity of basic fibroblast growth factor by suramin and related polyanions. British Journal of Cancer 69, 890-8.

Brown TA, Yang TM, Zaitsevskaia T, Xia Y, Dunn CA, Sigle RO, Knudsen B and Carter WG (2004) Adhesion or plasmin regulates tyrosine phosphorylation of a novel membrane glycoprotein p80/gp140/CUB domain-containing protein 1 in epithelia. J Biol Chem 279:14772-14783.

Cardinali M, Sartor O and Robbins KC (1992) Suramin, an experimental chemotherapeutic drug, activates the receptor for epidermal growth factor and promotes growth of certain malignant cells. J Clin Invest 89:1242-1247.

Casanova JE (2002) Epithelial cell cytoskeleton and intracellular trafficking V. Confluence of membrane trafficking and motility in epithelial cell models. Am J Physiol Gastrointest Liver Physiol 283:G1015-1019.

Chen JK, Falck JR, Reddy KM, Capdevila J and Harris RC (1998) Epoxyeicosatrienoic acids and their sulfonimide derivatives stimulate tyrosine phosphorylation and induce mitogenesis in renal epithelial cells. J Biol Chem 273:29254-29261.

Coffey RJ, Jr., Leof EB, Shipley GD and Moses HL (1987) Suramin inhibition of growth factor receptor binding and mitogenicity in AKR-2B cells. J Cell Physiol 132:143-148.

Counts RS, Nowak G, Wyatt RD and Schnellmann RG (1995) Nephrotoxicant inhibition of renal proximal tubule cell regeneration. Am J Physiol 269:F274-281.

Dhar, S., Gullbo, J., Csoka, K., Eriksson, E., Nilsson, K., Nickel, P., Larsson, R., and Nygren, P. (2000). Antitumor activity of suramin analogues in human tumour cell lines and primary cultures of tumour cells from patients. European Journal of Cancer 36, 803-809.

Eisenberger MA and Reyno LM (1994) Suramin. Cancer Treat Rev 20:259-273.

Firsching, A., Nickel, P., Mora, P., and Allolio, Bruno. (1995). Antiproliferative and angiostatic activity of suramin analogues. Cancer Research 55, 4957-4961.

Foekens JA, Sieuwerts AM, Stuurman-Smeets EM, Dorssers LC, Berns EM and Klijn JG (1992) Pleiotropic actions of suramin on the proliferation of human breast-cancer cells in vitro. Int J Cancer 51:439-444.

Fukata M, Nakagawa M and Kaibuchi K (2003) Roles of Rho-family GTPases in cell polarisation and directional migration. Curr Opin Cell Biol 15:590-597.

Fukuda K, Kawata S, Tamura S, Matsuda Y, Inui Y, Igura T, Inoue S, Kudara T and Matsuzawa Y (1998) Altered regulation of Src tyrosine kinase by transforming growth factor beta1 in a human hepatoma cell line. Hepatology 28:796-804.

Gagliardi, A.R.T., Kassack, M., Kreimeyer, A., Muller, G., Nickel, P., and Collins, D.C. (1998). Antiangiogenic and antiproliferative activity of suramin analogues. Cancer Chemother Pharmacol 41, 117-124.

Gill JS Connolly DC, McManus MJ, Maihle NJ and Windebank AJ (1996) Suramin induces phosphorylation of the high-affinity nerve growth factor receptor in PC12 cells and dorsal root ganglion neurons. J Neurochem 66:963-972.

Harder KW, Moller NP, Peacock JW and Jirik FR (1998) Protein-tyrosine phosphatase alpha regulates Src family kinases and alters cell-substratum adhesion. J Biol Chem 273:31890-31900.

Herbst RS (2004) Review of epidermal growth factor receptor biology. Int J Radiat Oncol Biol Phys 59:21-26.

Hosang M (1985) Suramin binds to platelet-derived growth factor and inhibits its biological activity. J Cell Biochem 29:265-273.

Kaur M, Reed E, Sartor O, Dahut W and Figg WD (2002) Suramin's development: what did we learn? Invest New Drugs 20:209-219.

Kays SE, Nowak G and Schnellmann RG (1996) Transforming growth factor-beta 1 inhibits regeneration of renal proximal tubular cells after oxidant exposure. J Biochem Toxicol 11:79-84.

Konety BR and Getzenberg RH (1997) Novel therapies for advanced prostate cancer. Semin Urol Oncol 15:33-42.

Kooistra A, Romijn JC and Schroder FH (1997) Stromal inhibition of epithelial cell growth in the prostate; overview of an experimental study. Urol Res 25:S97-105.

Kreimeyer, A., Muller, G., Kassack, M., Nickel. P., and Gagliardi, A.R.T. (1998). Sulfanilic Acid-, benzenedisulfonic acid-, and naphthalenetrisulfonic acid analogues. Arch. Pharm. Pharm. Med. Chem. 331, 97-103.

Kyosseva SV (2004) Mitogen-activated protein kinase signaling. Int Rev Neurobiol 59:201-220.

Leu TH and Maa MC (2003) Functional implication of the interaction between EGF receptor and c-Src. Front Biosci 1:s28-38.

Liu Y, Bishop A, Witucki L, Kraybill B, Shimizu E, Tsien J, Ubersax J, Blethrow J, Morgan DO and Shokat KM (1999) Structural basis for selective inhibition of Src family kinases by PP1. Chem Biol 6:671-678.

Lokshin A, Peng X, Campbell PG, Barsouk A and Levitt ML (1999) Mechanisms of growth stimulation by suramin in non-small-cell lung cancer cell lines. Cancer Chemother Pharmacol 43:341-347.

Maeshima A, Nojima Y and Kojima I (2002) Activin A: an autocrine regulator of cell growth and differentiation in renal proximal tubular cells. Kidney Int 62:446-454.

Manganini M and Maier JA (2000) Transforming growth factor beta2 inhibition of hepatocyte growth factor-induced endothelial proliferation and migration. Oncogene 19:124-133.

Marchetti, D., Reiland, J., Erwin, B., and Roy, M. (2003). Inhibition of heparanase activity and heparanase-induced angiogenesis by suramin analogues. Int. J. Cancer 104, 167-174.

McCain DF, Wu L, Nickel P, Kassack MU, Kreimeyer A, Gagliardi A, Collins DC and Zhang ZY (2004) Suramin derivatives as inhibitors and activators of protein-tyrosine phosphatases. J Biol Chem 279:14713-14725.

Meyers, M.O., Gagliardi, A.R., Flattmann, G. J., Su, J.L., Wang, Y.Z., and Woltering, E.A.(2000) Suramin analogs inhibit human angiogenesis in vitro. J. Surg. Res. 91,130-134.

Nakata H (2004) Stimulation of extracellular signal-regulated kinase pathway by suramin with concomitant activation of DNA synthesis in cultured cells. J Pharmacol Exp Ther 308:744-753.

Nowak G and Schnellmann RG (1995) Improved culture conditions stimulate gluconeogenesis in primary cultures of renal proximal tubule cells. Am J Physiol 268:C1053-1061.

Nowak G and Schnellmann RG (1996) L-ascorbic acid regulates growth and metabolism of renal cells: improvements in cell culture. Am J Physiol 271:C2072-2080.

Nowak G and Schnellmann RG (1997) Renal cell regeneration following oxidant exposure: inhibition by TGF-beta1 and stimulation by ascorbic acid. Toxicol Appl Pharmacol 145:175-183.

Richardson CJ, Schalm SS and Blenis J (2004) PI3-kinase and TOR: PIKTORing cell growth. Semin Cell Dev Biol 15:147-159.

Rodeheaver DP, Aleo MD and Schnellmann RG (1990) Differences in enzymatic and mechanical isolated rabbit renal proximal tubules: comparison in long-term incubation. In Vitro Cell Dev Biol 26:898-904.

Roskoski R, Jr. (2004) Src protein-tyrosine kinase structure and regulation. Biochem Biophys Res Commun 324:1155-1164.

Sponsel HT, Breckon R, Hammond W and Anderson RJ (1994) Mechanisms of recovery from mechanical injury of renal tubular epithelial cells. Am J Physiol 267:F257-264.

Stein CA (1993) Suramin: a novel antineoplastic agent with multiple potential mechanisms of action. Cancer Res 53:2239-2248.

Toback FG (1992) Regeneration after acute tubular necrosis. Kidney Int 41:226-246.

Wade TP, Kasid A, Stein CA, LaRocca RV, Sargent ER, Gomella LG, Myers CE and Linehan WM (1992) Suramin interference with trans-

(56) References Cited

OTHER PUBLICATIONS forming growth factor-beta inhibition of human renal cell carcinoma in culture. J Surg Res 53:195-198.

Wang JY and Williams LT (1984) A v-sis oncogene protein produced in bacteria competes for platelet-derived growth factor binding to its receptor. J Biol Chem 259:10645-10648.

Yamashita et al., Activin A Is a Potent Activator of Renal Interstital Fibroblasts. J Am Soc Nephrol 15: 91-101, 2004.

Zheng XM, Resnick RJ and Shalloway D (2000) A phosphotyrosine displacement mechanism for activation of Src by PTPalpha. Embo J 19:964-978.

Zhuang S, Dang Y and Schnellmann RG (2004) Requirement of the epidermal growth factor receptor in renal epithelial cell proliferation and migration. Am J Physiol Renal Physiol 287:F365-F372.

Zhuang S, Schnellmann RG. Suramin promotes proliferation and scattering of renal epithelial cells. J Pharmacol Exp Ther. Jul. 2005;314(1):383-90. Epub Apr. 15, 2005.

Liu et al., "Suramin inhibits renal fibrosis in chronic experimental kidney disease," *Journal of the American Society of Neprhology*, date of submission: Jan. 27, 2011.

Zhuang et al., "Suramin promotes recovery from renal ischemia/reperfusion injury in mice," *Kidney International*, 75:304-311, doi:10.1038/ki.2008.506, 2008.

\* cited by examiner

| Control | Suramin |
|---|---|
|  |  |
| EGF | Suramin + EGF |
|  |  |

CELL REPAIR AND REGENERATION BY SURAMIN AND RELATED POLYSULFONATED NAPTHYLUREAS

CROSS-REFERENCE TO RELATED APPLICATIONS

This application claims benefit of U.S. Provisional Application No. 60/759,118, filed Jan. 12, 2006, which is hereby incorporated herein by reference in its entirety.

STATEMENT REGARDING FEDERALLY SPONSORED RESEARCH

This invention was made with government support under Grant ES-04410 awarded by The National Institutes of Health. The government has certain rights in the invention.

BACKGROUND

Ischemia is a feature of heart, kidney, liver, and intestinal diseases, transient ischemic attacks, cerebrovascular accidents, ruptured arteriovenous malformations, and peripheral artery occlusive disease. In contrast to hypoxia, which is a more general term denoting a shortage of oxygen (usually a result of lack of oxygen in the air being breathed), ischemia is an absolute or relative shortage of the blood supply to an organ. Relative shortage means the mismatch of blood supply (oxygen delivery) and blood request for adequate oxygenation of tissue. Ischemia can also be described as an inadequate flow of blood to a part of the body, caused by constriction or blockage of the blood vessels supplying it. Since oxygen is mainly bound to hemoglobin in red blood cells, insufficient blood supply causes tissue to become hypoxic, or, if no oxygen is supplied at all, anoxic. This can cause necrosis (i.e. cell death).

Tissues especially sensitive to inadequate blood supply are the heart, liver, kidneys, and brain. Ischemia in brain tissue, for example due to stroke or head injury, causes a process called the ischemic cascade to be unleashed, in which proteolytic enzymes, reactive oxygen species, and other harmful chemicals damage and may ultimately kill brain tissue.

Restoration of blood flow after a period of ischemia can actually be more damaging than the ischemia. Reintroduction of oxygen causes a greater production of damaging free radicals, resulting in reperfusion injury. With reperfusion injury, necrosis can be greatly accelerated.

Disclosed herein are compositions and methods to stimulate repair and regeneration of injured tissue, such as tissue damaged from ischemia. For example, the disclosed compositions and methods are efficacious in the treatment of acute brain injury due to stroke, spinal cord injury due to compression, acute cardiac injury due to ischemia, and acute liver or kidney injury due to drug or toxicant exposure or ischemia.

BRIEF SUMMARY

In accordance with the purpose of this invention, as embodied and broadly described herein, this invention relates to compositions and methods for promoting tissue repair and regeneration. Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 3 shows blockade of the EGF receptor by AG1478 inhibits EGF-induced RPTC proliferation and scattering but not suramin-induced RPTC proliferation and scattering.

FIG. 5 shows effects of PI3K and ERK1/2 pathway inhibitors on RPTC proliferation and scattering following plating and suramin exposure.

FIG. 7 shows effects of Src inhibition on RPTC proliferation and scattering following plating and suramin exposure.

DETAILED DESCRIPTION

Figure 1A:
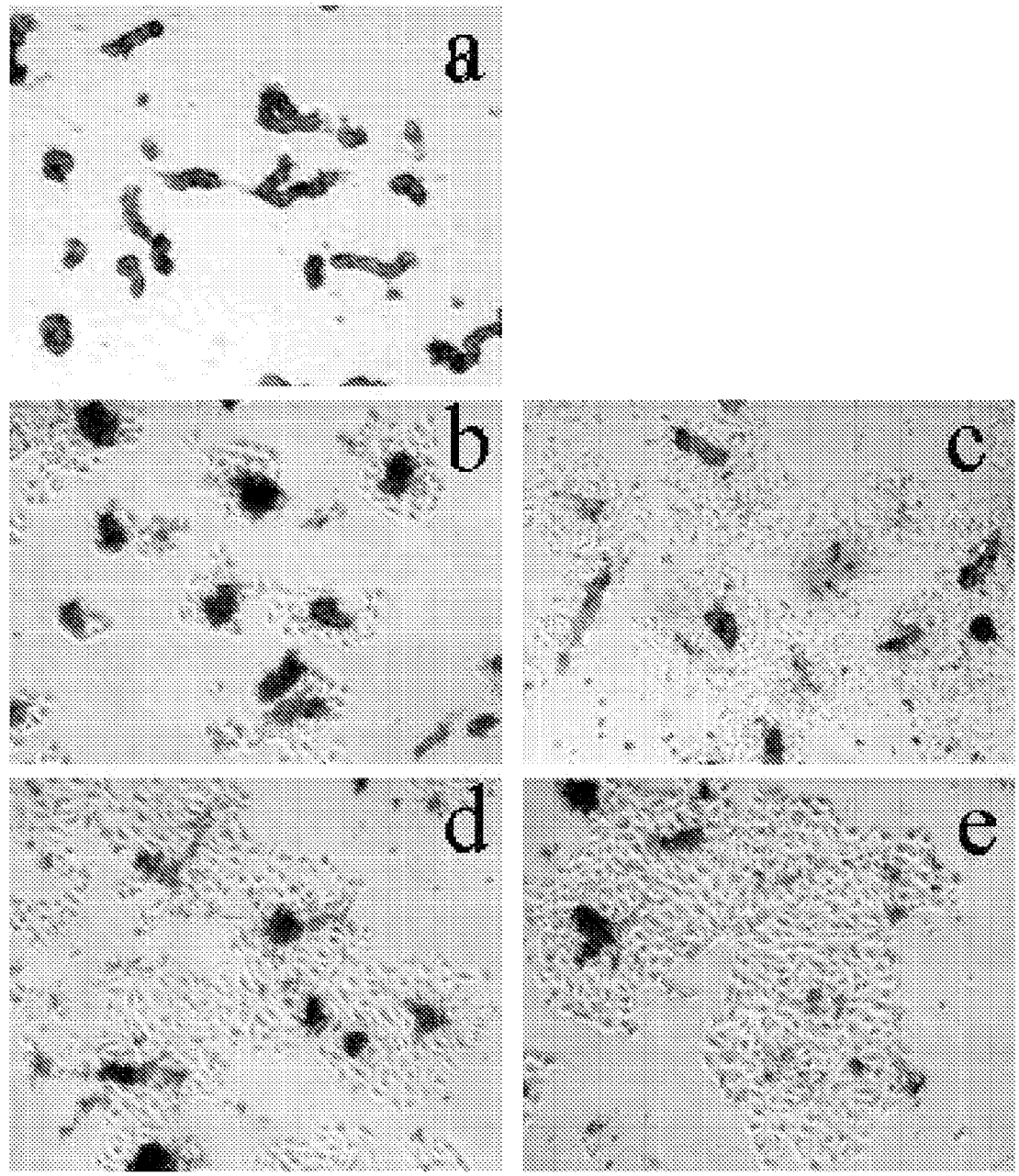
FIG. 1 shows promotion of RPTC outgrowth and proliferation. Renal proximal tubules were plated (Aa) and after 24 hr exposed to fresh medium alone (Ab), 50 µM suramin (Ac), 10 ng/ml EGF (Ad), or suramin+EGF (Ae) for 24 hr and then photographed. RPTC were cultured for 3 days, and then incubated with the above agents (B) or varying concentrations of suramin (C) for 24 hr. After staining with propidium iodide, cell cycle was analyzed by flow cytometry and the number of cells in S-phase determined. Data are expressed as means+SEM, n=3. Bars with different superscripts are significantly from each other (p<0.05).

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and discussed and a number of modifications that can be made to a number of molecules including the compound are discussed, each and every combination and permutation of compound and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Method of Promoting Tissue Repair/Regeneration

Provided herein is a method of promoting tissue repair and/or regeneration in a subject, comprising administering to a subject in need of tissue repair and/or regeneration a composition comprising a therapeutically effective amount of suramin or an analogue or derivative thereof. The disclosed composition can stimulate cell migration and proliferation, thereby accelerating repair, regeneration, and recovery of function.

The subject in need of tissue repair and/or regeneration is one who has been injured. "Injury" or "injured" as used herein refers to measurable damage to tissue resulting from mechanical forces (i.e., trauma), drugs, toxicants, endotoxin, or ischemia. As used herein, "repair" refers to measurable, directed improvement of damaged tissue.

The tissue can be damaged from an ischemic injury. The ischemic injury can be due to neural ischemia. The ischemic injury can be due to spinal cord ischemia. The ischemic injury can be due to cardiac ischemia. The ischemic injury can be due to hepatic ischemia. The ischemic injury can be due to renal ischemia. The tissue can be damaged from a laceration or abrasion.

In some aspects of the method, tissues that can be repaired by the disclosed composition can undergoes proliferation during repair. Thus, in some aspects of the method, the tissue is an epithelial tissue. Thus, provided is a method or promoting epithelial tissue repair and/or regeneration in a subject, comprising administering to a subject in need of tissue repair and/or regeneration a composition comprising a therapeutically effective amount of suramin or an analogue or derivative thereof.

In some aspects of the method, the suramin derivative promotes activation of PI3K in renal proximal tubule cells.

In some aspects of the method, the tissue does not comprise a cancer or tumor.

B. Ischemia

In some aspects, the subject has been diagnosed with an ischemic injury. The ischemic injury can be due to neural ischemia. The ischemic injury can be due to spinal cord ischemia. The ischemic injury can be due to cardiac ischemia. The ischemic injury can be due to hepatic ischemia. The ischemic injury can be due to renal ischemia. In some aspects, the subject has been diagnosed with a dermal laceration or abrasion. In some aspects, the subject has been diagnosed with a corneal laceration or abrasion.

The method can further comprise monitoring the subject for tissue repair. This can involve monitoring the subject for improved pathology or function. For example, in acute renal failure the subject can be monitored using blood analysis (e.g. creatinine, electrolytes, osmolality) or urine analysis (e.g. electrolytes, proteins). Heart and Liver function an be monitored by routine clinical measurements. Spinal cord injury repair can be monitored by motor function. Dermal and corneal injury can be monitored by visual inspection.

1. Stroke

A stroke, also known as cerebrovascular accident (CVA), is an acute neurological injury in which the blood supply to a part of the brain is interrupted. That is, a stroke involves the sudden loss of neuronal function due to disturbance in cerebral perfusion. This disturbance in perfusion is commonly arterial, but can be venous. The part of the brain with disturbed perfusion no longer receives adequate oxygen. This initiates the ischemic cascade which causes brain cells to die or be seriously damaged, impairing local brain function. Risk factors include advanced age, hypertension (high blood pressure), diabetes mellitus, high cholesterol, and cigarette smoking.

Strokes can be classified into two major categories: ischemic and hemorrhagic. Ischemia can be due to thrombosis, embolism, or systemic hypoperfusion. Hemorrhage can be due to intracerebral hemorrhage or subarachnoid hemorrhage. ~80% of strokes are due to ischemia. In an ischemic stroke, which is the cause of approximately 85-90% of strokes, a blood vessel becomes occluded and the blood supply to part of the brain is totally or partially blocked. Ischemic stroke is commonly divided into thrombotic stroke, embolic stroke, systemic hypoperfusion (Watershed or Border Zone stroke), or venous thrombosis.

2. Spinal Cord Compression

Spinal cord compression develops when the spinal cord is compressed by a tumor, abscess or other lesion, or by physical trauma. It is regarded as a medical emergency independent of its cause, and requires swift diagnosis and treatment to prevent long-term disability due to irreversible spinal cord injury.

3. Cardiac Ischemia

Cardiac ischemia is a situation in which the flow of oxygen-rich blood to the heart muscle is impeded, resulting in inadequate oxygenation of the heart. The most common cause of cardiac ischemia is plaque buildup in the arteries due to the long-term effects of coronary artery disease. This plaque buildup narrows the arteries to the point where the amount of blood flowing through the arteries is not enough to supply oxygen-rich blood to the heart, especially during times of physical exertion or emotional stress.

The lack of oxygen is often temporary, and symptoms can include a type of chest pain, pressure or discomfort called angina. These episodes may last anywhere between 2 and 20 minutes. However, many episodes of ischemia do not have any associated symptoms (silent ischemia).

Lengthy episodes of cardiac ischemia can be a sign of a heart attack. A heart attack occurs when a blood clot blocks the flow of blood to the heart muscle. It can occur in an artery already narrowed by plaque (atherosclerosis), or a heart attack can occur after a blood clot breaks off from its original site and travels through the arteries. The blockage causes a sudden and possibly complete interruption of oxygen-rich blood flow, and the resulting heart attack could cause permanent damage and scarring to the portion of the heart muscle supplied by the blocked artery.

4. Kidney Ischemia

Renal ischemia, also called nephric ischemia, is the deficiency of blood in one or both kidneys, or nephrons, usually due to functional constriction or actual obstruction of a blood vessel. Ischemia/reperfusion (I/R) injury of the kidney is a common cause of acute renal failure (ARF) and is associated with high morbidity and mortality in the intensive care unit.

C. Mechanical Injury

As used herein, mechanical tissue injury can result from, for example, a scrape, cut, laceration wound, crush wound, compression wound, stretch injury, bite wound, graze, bullet wound, explosion injury, body piercing, stab wound, burn wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, or ischemic injury.

D. Suramin

As disclosed herein, Suramin, a polysulfonated naphthylurea, promotes the proliferation and migration of epithelial cells. Also as disclosed herein, suramin is effective in the treatment of acute or chronic diseases that are associated with cell death and loss. For example, suramin is disclosed herein to be efficacious in the treatment of acute brain injury due to stroke, spinal cord injury due to compression, acute cardiac injury due to ischemia, and acute liver or kidney injury due to drug or toxicant exposure or ischemia. Under these conditions, suramin would stimulate cell repair and regeneration and promote the return of normal organ function. In addition, it can be used topically to promote wound healing. This approach is unique in that it can repair already damaged tissues.

Also disclosed are suramin derivatives and analogues for use in the disclosed methods. Derivatives of suramin as known in the art. See U.S. Pat. No. 5,173,509, Braddock, P S., et al. 1994; Dhar, S., et al. 2000; Firsching, A., et al. 1995; Gagliardi, A. R. T., et al. 1998; Kreimeyer, A., et al. 1998; Marchetti, D., et al. 2003; McCain, D. F., et al. 2004; Meyers, M. O., et al. 2000; which are each incorporated herein by reference for their teaching of a suramin derivatives.

Also provided is a method of promoting tissue repair and/or regeneration in a subject, comprising administering to a subject in need of tissue repair and/or regeneration a composition comprising a therapeutically effective amount of a compound comprising the structure, necessary that $R^{2a}$ and $R^{2b}$ have the same structure, and both aspects including the same and different structures are intended.

It is also contemplated that the compounds can be further substituted. It should be understood that a hydrogen can be replaced with one or more substituents, as described herein.

In various aspects, $R^{1a}$ and/or $R^{1b}$ are substituted naphthalene, aniline or phenyl, such as, for example, aminonaphthalene-4,6,8-trisulfonic acid, aminonaphthalene-3,6,8-trisulfonic acid, aniline-3-sulfonic acid, aniline-4-sulfonic acid, aniline-2,4-disulfonic acid, aniline-2,5-disulfonic acid, aniniline-3-phosphonic acid, aniline-4-phosphonic acid, 4-methylaniline-3-phosphonic acid, or phenyl sulfonic acid. In other aspects, $R^{1a}$ and/or $R^{1b}$ are substituted alkyl, such as, for example, ethylamine-2-sulfonic acid or ethylamine-2-phosphonic acid. In a specific aspect, both $R^{1a}$ and/or $R^{1b}$ are aminonaphthalene-trisulfonic acid.

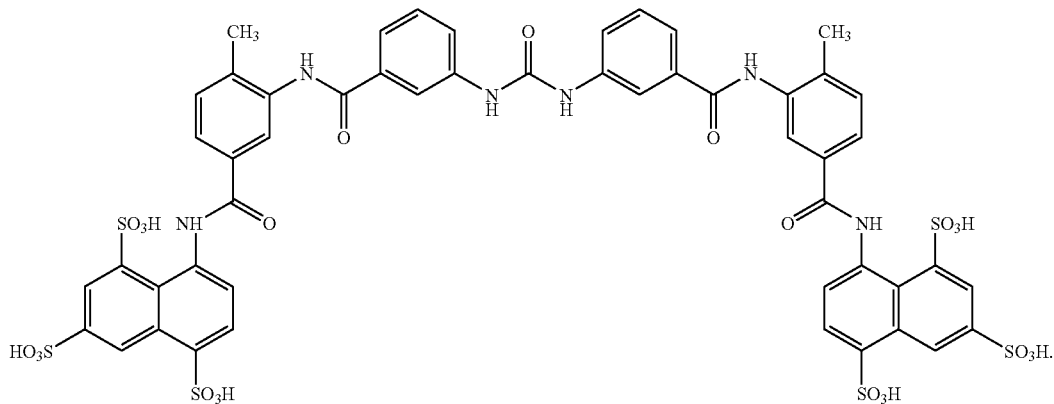 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1]

Also provided is a method of promoting tissue repair and/or regeneration in a subject, comprising administering to a subject in need of tissue repair and/or regeneration a composition comprising a therapeutically effective amount of a compound comprising the structure,

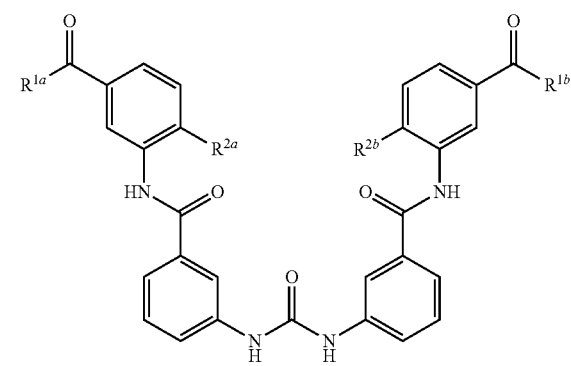

for example, suramin, derivatives thereof, salts thereof, and mixtures thereof, wherein $R^{1a}$ and $R^{1b}$ are, independently, hydrogen, hydroxyl, alkyl, aryl, alkoxy, carboxyl, ester, ester, amino, or amide, and wherein $R^{2a}$ and $R^{2b}$ are, independently, hydrogen, hydroxyl, alkyl, aryl, acyl, alkoxy, carboxyl, ester, ester, amino, amide, or halide. It is not necessary that $R^{1a}$ and $R^{1b}$ have the same structure, and both aspects including the same and different structures are intended. Likewise, it is not In one aspect, $R^{2a}$ and/or $R^{2b}$ are alkyl, such as, for example, methyl, ethyl, propyl, isopropyl, butyl, tert-butyl. In another aspect, $R^{2a}$ and/or $R^{2b}$ are halogen, such as, for example, fluoro. In another aspect, $R^{2a}$ and/or $R^{2b}$ are acyl, such as, for example, methylbenzoyl or ethylbenzoyl. In yet another aspect, $R^{2a}$ and/or $R^{2b}$ are alkoxy, such as, for example, methoxymethyl. In a preferred aspect, both $R^{2a}$ and $R^{2b}$ are lower alkyl, such as, for example, methyl.

In one aspect, both $R^{1a}$ and/or $R^{1b}$ are aminonaphthalene-trisulfonic acid and both $R^{2a}$ and $R^{2b}$ are methyl.

In certain aspects, the compounds can comprise one or more ionizable functional groups, such as, for example, aminonaphthalene-trisulfonic acid. Suitable ionizable groups include sulfonic acid, carboxylic acid, and the like. The ionizable functional groups of a specific suramin compound can be present in the form of an acid, a salt, or a combination thereof. In one aspect, the ionizable functional groups, such as sulfonic acids, are present in acidic form. In another aspect, the ionizable functional groups, such as sulfonic acids, are present in salt form, such as, for example, a sodium salt, a potassium salt, or an ammonium salt. In a specific aspect, the suramin compound comprises a hexasodium salt.

It is further contemplated that the suramin compound and various derivatives disclosed herein can be further substituted and any such substitutions are included.

Suramin compounds are known in the art and are commercially available (Sigma-Aldrich, St. Louis, Mo., USA). One of skill in the art can readily select and/or prepare appropriate suramin compounds for use in the present invention.

E. Pharmaceutical Carriers

The disclosed compositions can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

F. Methods of Administration

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like. In some aspects, the composition is not administered systemically, such as orally. For example, in some aspects, the composition can be applied topically to the eyes, skin, mucosal surfaces, or wounds.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the disclosed composition comprising suramin used alone might range from about 1 µg/kg to up to 100 mg/kg of body weight or more per day, depending on the factors mentioned above. For example, the disclosed composition comprising suramin can be administered from about 0.3 mg/kg to about 10 mg/kg when given parentally. For example, the disclosed composition comprising suramin can be administered from about 50 to about 100 micromolar when given topically.

Following administration of a disclosed composition for treating tissue injury, the efficacy of the therapeutic composition comprising suramin can be assessed in various ways well known to the skilled practitioner. For instance, one of ordinary skill in the art will understand that a composition disclosed herein is efficacious in treating tissue injury in a subject by observing that the composition promotes repair, regeneration, and/or function of the tissue.

The disclosed compositions and methods can also be used for example as tools to isolate and test new drug candidates for a variety of tissue injuries.

G. Uses

The disclosed compositions can be used in a variety of ways as research tools. Other uses are disclosed, apparent from the disclosure, and/or will be understood by those in the art.

H. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a compound" includes a plurality of such compounds, reference to "the compound" is a reference to one or more compounds and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "effective amount" refers to such amount as is capable of performing the function of the compound or property for which an effective amount is expressed. As will be pointed out below, the exact amount required will vary from process to process, depending on recognized variables such as the compounds employed and the processing conditions observed. Thus, it is not typically possible to specify an exact "effective amount." However, an appropriate effective amount may be determined by one of ordinary skill in the art using only routine experimentation. In various aspects, an amount can be therapeutically effective; that is, effective to treat an existing disease or condition. In further various aspects, a preparation can be prophylactically effective; that is, effective for prevention of a disease or condition. In a further aspect, a compound or moiety can be provided in an amount effective to perform an imaging function.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example 1 to 12 carbon atoms or 1 to 6 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included in the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkynyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula NA$^1$A$^2$A$^3$, where A$^1$, A$^2$, and A$^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula C(O)OH.

The term "ester" as used herein is represented by the formula —OC(O)A$^1$ or —C(O)OA$^1$, where A$^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is the term used to describe a group that is produced, for example, by the reaction between a compound having at least two carboxylic acid groups with a compound having at least two hydroxyl groups.

The term "ether" as used herein is represented by the formula A$^1$OA$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine. It is also contemplated that pseudo-halides, such as, for example, tosylate, mesylate, brosylate, and the like, can be substituted halides.

The term "hydroxyl" as used herein is represented by the formula —OH.

The term "ketone" as used herein is represented by the formula A$^1$C(O)A$^2$, where A$^1$ and A$^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

I. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Suramin Promotes Proliferation and Scattering of Renal Epithelial Cells i. Abstract Primary cultures of renal proximal tubules are known to recapitulate several early events in the process of renal regeneration following injury. In this study, we demonstrate that suramin, a polysulfonated naphthylurea, stimulates outgrowth, scattering and proliferation of primary cultures of renal proximal tubule cells (RPTC). These responses were comparable to those produced by epidermal growth factor (EGF). However, AG1478, a specific inhibitor of the EGF receptor, blocked EGF, but not suramin-induced RPTC outgrowth, scattering and proliferation. Suramin stimulated phosphorylation of Akt, a downstream kinase of phosphoinositide-3-kinase (PI3K), extracellular signaling regulated kinase 1/2 (ERK1/2) and Src, but not the EGF receptor. Blockade of Src, but not the EGF receptor, inhibited Akt and ERK1/2 phosphorylation. Further, inactivation of PI3K with LY294002 blocked suramin-induced RPTC outgrowth, scattering and proliferation while blockade of ERK1/2 had no effect. These data identify novel effects of suramin in RPTC outgrowth, scattering and proliferation. Further, suramin-induced outgrowth, scattering and proliferation of RPTC is through Src mediated activation of the PI3K pathway, but not ERK1/2 or the EGF receptor.

Suramin is a hexasulfonated, polyaromatic compound that has been used in the prevention and treatment of early stages of human trypanosomiasis (Barrett et al., 2003) It also has antitumor activity in numerous types of cancer cells in culture and in cancer xenograft models (Stein, 1993). Although the molecular basis of the antitumor effects of suramin is not completely understood, interruption of autocrine growth factor loops may be responsible. For example, it has been demonstrated that suramin can inhibit the binding of multiple growth factors to their receptors. These growth factors include epidermal growth factor (EGF), platelet-derived growth factor (PDGF), fibroblast growth factor (FGF), and insulin growth factor II (IGFII) (Wang and Williams, 1984; Hosang, 1985; Betsholtz et al., 1986; Coffey et al., 1987). In addition, suramin blocks the interaction of transforming growth factor-β (TGF-β) with its receptor; TGF-β exerts a growth inhibitory effect in most of cell types including renal epithelial cells (Wade et al., 1992; Sponsel et al., 1994; Nowak and Schnellmann, 1997).

Although suramin is effective when it is used as a chemotherapeutic agent for treatment of some tumors (e.g. prostate cancer) (Konety and Getzenberg, 1997), its antitumor activity has not proven successful in all tumors tested (Eisenberger and Reyno, 1994; Kaur et al., 2002) One explanation for this finding is that suramin may induce other biological actions that are in conflict with its antitumor effect. Indeed, suramin can induce proliferation in certain cancer cell lines, in particular, epithelial tumor cell lines with high expression of the EGF receptor (e.g. A431 cells) (Cardinali et al., 1992) and non-small-cell lung cancer cells (Lokshin et al., 1999). Further, suramin stimulates proliferation of several non-tumor cell lines such as Chinese hamster ovary (CHO) cells (Nakata, 2004). Study of the mechanisms of such proliferation has suggested that suramin may activate the EGF receptor by stimulating the release of TGFα, an EGF receptor ligand (Cardinali et al., 1992) or directly induce EGF receptor dimerization (Lokshin et al., 1999).

Activation of the EGF receptor leads to multiple intracellular signaling events (Herbst, 2004). Among the signaling enzymes mediating proliferation, phosphoinositide-3-kinase (PI3K), and extracellular signaling regulated kinase 1/2 (ERK1/2) pathways have been reported to be activated by suramin and required for the mitogenic response in CHO cells (Nakata, 2004).

Src is a non receptor tyrosine kinase that plays an important role in mediating a variety of cellular functions by delivering a signal to downstream effectors including the PI3K and ERK1/2 pathways. Src activity is tightly controlled by phosphorylation of two tyrosine sites, activation by phosphorylation of tyrosine 416 and inactivation by phosphorylation of tyrosine 527 (Roskoski, 2004). A recent study showed that suramin also can stimulate Src phosphorylation in keratinocytes (Brown et al., 2004). The role of Src in suramin-mediated biological responses remains to be determined.

Recent studies showed that RPTC proliferate and migrate in an EGF receptor-dependent manner in the absence of exogenous growth factors (Zhuang et al., 2004), suggesting involvement of autocrine mechanisms in this process. Since suramin has been reported to block the interaction of growth factors with their receptors and thereby inhibit cell proliferation (Wang and Williams, 1984; Hosang, 1985; Betsholtz et al., 1986; Coffey et al., 1987; Anderson and Ray, 1998), our initial attempt was to assess the autocrine mechanism of RPTC proliferation and migration using suramin. Unexpectedly, suramin stimulated RPTC outgrowth, scattering and proliferation and the signaling pathways for these actions were investigated.

ii. Materials and Methods

Chemicals and reagents: Human recombinant EGF was obtained from R & D systems (Minneapolis, Minn.). 2-(4-Morpholinyl)-8-phenyl-4H-1-benzopyran-4-one (LY 294002) and 1,4-Diamino-2,3-dicyano-1,4-bis(2-aminophenylthio)butadiene (U0126) were purchased from Cell Signaling Technology (Beverly, Mass.). 4-(3-chloroanilino)-6,7-dimethoxyquinazoline (AG1478) was obtained from Biomol (Plymouth Meeting, Pa.). All other chemicals were purchased from Sigma (St. Louis, Mo.). Antibodies to phospho-EGF receptor, phospho-Akt (Tyr 473), Akt, phospho-ERK1/2 (Thr202/Tyr204), phospho-Src (Tyr 416 or Tyr527) and Src were obtained from Cell Signaling Technology (Beverly, Mass.). Antibodies to ERK1/2 and EGF receptor were purchased from BD Laboratories (San Diego, Calif.) and Santa Cruz (Santa Cruz, Calif.), respectively. Fluorescein-labeled phalloidin was obtained from Molecular probes (Eugene, Oreg.).

Isolation and culture of renal proximal tubules: Isolation and culture of renal proximal tubules were performed as described previously (Rodeheaver et al., 1990; Nowak and Schnellmann, 1995; Nowak and Schnellmann, 1996). Female New Zealand White rabbits (1.5-2.5 kg) were purchased from Myrtle's Rabbitry (Thompson Station, Tenn.). RPTC were isolated using the iron oxide perfusion method and grown in 6-well tissue culture dishes under improved conditions. The culture medium was an 1:1 mixture of DMEM/Ham's F-12 (without glucose, phenol red, or sodium pyruvate) supplemented with 15 mM HEPES buffer, 2.5 mM L-glutamine, 1 µM pyridoxine HCl, 15 mM sodium bicarbonate, and 6 mM lactate. Hydrocortisone (50 µM), selenium (5 ng/ml), human transferrin (5 µg/ml) bovine insulin (10 nM) and L-ascorbic acid-2-phosphate (50 µM) were added daily to fresh culture medium.

Isolated tubules were plated at 1 mg protein/well in a 6-well plate. On day 2, RPTC were incubated in the presence and absence of various pharmacological inhibitors for different time periods as indicated in the figure legends. For some experiments, suramin was added to RPTC on day 3 and then incubated for 24 hr in the presence or absence of various inhibitors before samples were taken.

MTT assay: The 3-(4,5-dimethylthiazol-2-yl)-2,5-diphenyl-tetrazolium bromide (MTT) assay was used to assess cell proliferation (Kooistra et al., 1997; Maeshima et al., 2002). Following a 48 hr exposure to various inhibitors or diluents, MTT was added (final concentration of 0.5 mg/ml) to individual cultures for an additional 30 min. Tetrazolium was released by dimethyl sulfoxide and optical density was determined with a spectrophotometer (570 nm). Data were normalized to diluent-treated cultures.

Cell cycle analysis: Cell cycle phase was determined using flow cytometry as previously described (Zhuang et al., 2004). Cells were harvested, stained with propidium iodide and the number of cells in S-phase of cell cycle determined.

Preparation of cell lysates and immunoblot analysis: After different treatments, RPTC were washed twice with PBS and harvested in lysis buffer (0.25 M Tris-HCl, pH 6.8, 4% SDS, 10% glycerol, 1 mg/ml bromophenol blue, and 0.5% 2-mercaptoethanol). Cells were disrupted by sonication for 15 seconds and lysates stored at −20o C. Equal amounts of cellular protein lysate were separated on 10% polyacrylamide gels and transferred to nitrocellulose membranes. After treatment with 5% skim milk at 4oC overnight, membranes were incubated with various antibodies for 1 hr, and then incubated with an appropriate horseradish-peroxidase conjugated secondary antibody (Amersham, Piscataway, N.J.). Bound antibodies were visualized following chemiluminescence detection on autoradiographic film.

Immunocytochemistry: After various treatments, RPTC were fixed with 10% buffered formalin, washed, permeabilized, and blocked with BSA. Fluorescein conjugated phalloidin was added and RPTC visualized by fluorescent microscopy.

Statistical analysis: Renal proximal tubules isolated from an individual rabbit represents a single experiment (n=1) consisting of data obtained from three wells. Data are presented as means+SEM and were subjected to one-way ANOVA. Multiple means were compared using Tukey's test. $P<0.05$ was considered a statistically significant difference between mean values.

iii. Results

Suramin induces RPTC outgrowth, scattering and proliferation: We previously developed primary cultures of RPTC in which isolated tubules are plated, RPTC grow out from the tubules and proliferate to form a monolayer in six days in the absence of exogenous growth factor stimulation (Nowak and Schnellmann, 1995). Outgrowth, scattering and proliferation of RPTC from the tubule fragments were observed within three days of plating and reached confluence at six days (FIG. 1A and data not shown). Using this system, we recently showed that the EGF receptor is activated and is required for RPTC proliferation and migration following plating (Zhuang et al., 2004), suggesting autocrine production of EGF receptor ligands is involved in the activation of the EGF receptor and RPTC proliferation.

Because suramin has been reported to inhibit the growth promoting effects of conditioned media following injury of a renal epithelial cell line (Anderson and Ray, 1998), we examined whether suramin exerted the same effect on RPTC proliferation following plating. Surprisingly, the addition of suramin stimulated RPTC outgrowth (FIG. 1, Panel A). Consistent with our previous observations (Zhuang et al., 2004), exogenous EGF promoted RPTC outgrowth. However, co-incubation of suramin with EGF did not further stimulate RPTC outgrowth. Thus, suramin potentiated outgrowth of RPTC from isolated renal proximal tubules and had no effect on EGF-induced RPTC outgrowth.

Figure 1B:
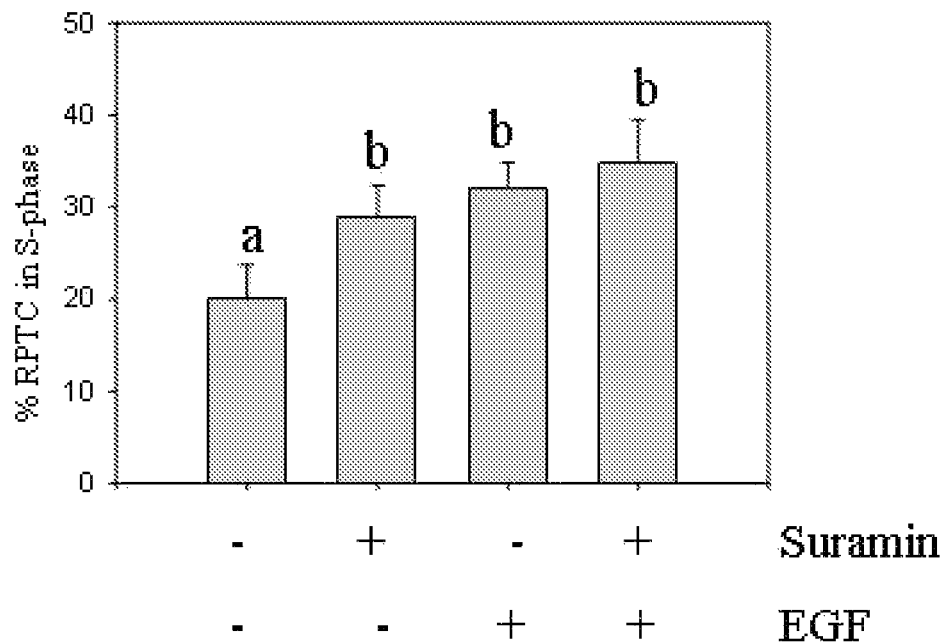
Figure 1C:
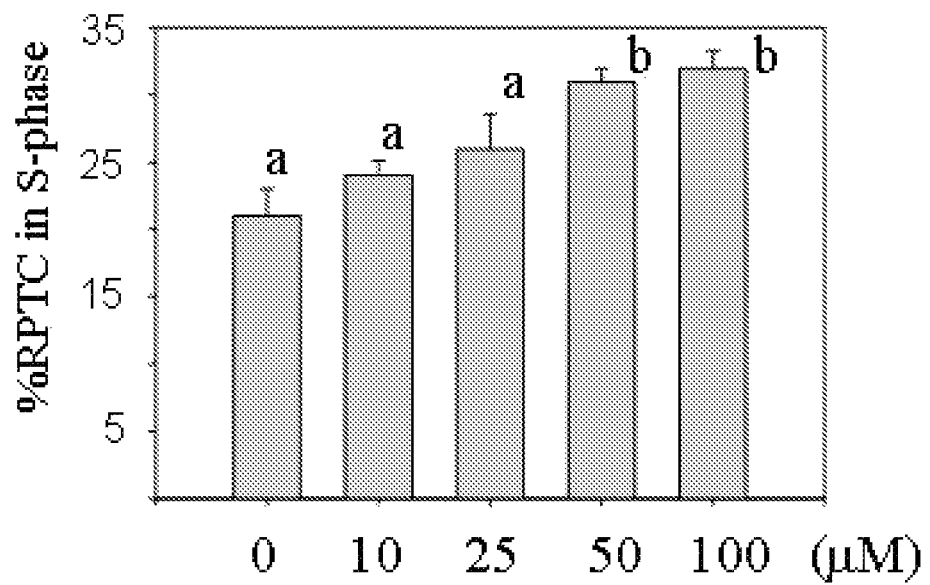
Figure 5A:
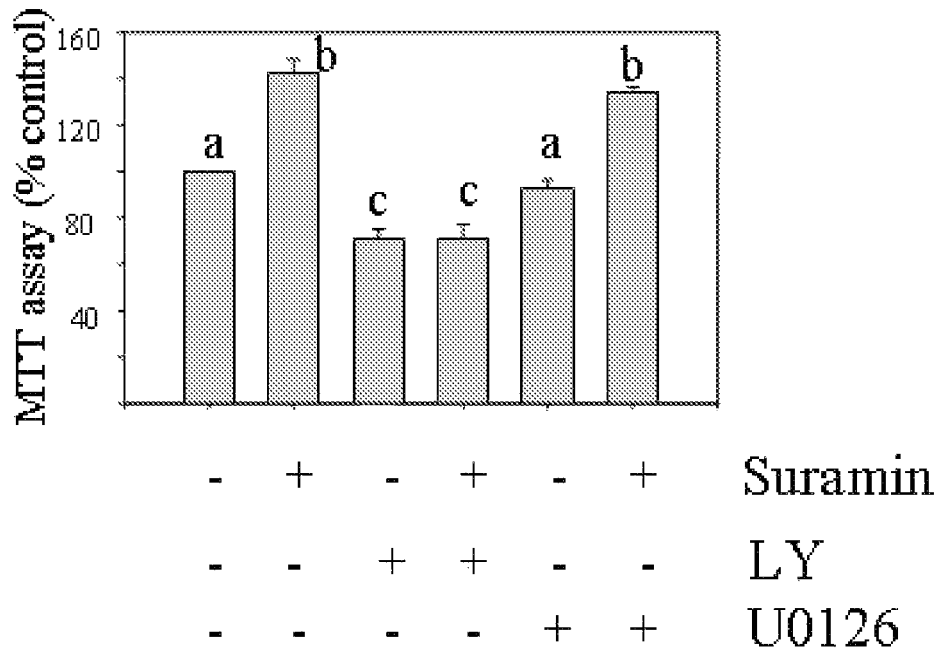
FIG. 5A shows RPTC cultured for 2 days and then incubated with 50 µM suramin for 48 hr in the presence and absence of 20 µM LY294002 (LY) and 10 µM U0126. Cell proliferation was determined using the MTT assay. Data are expressed as means+SEM of the percentage of MTT activity compared to controls grown with diluent (N=3).
Figure 5B:
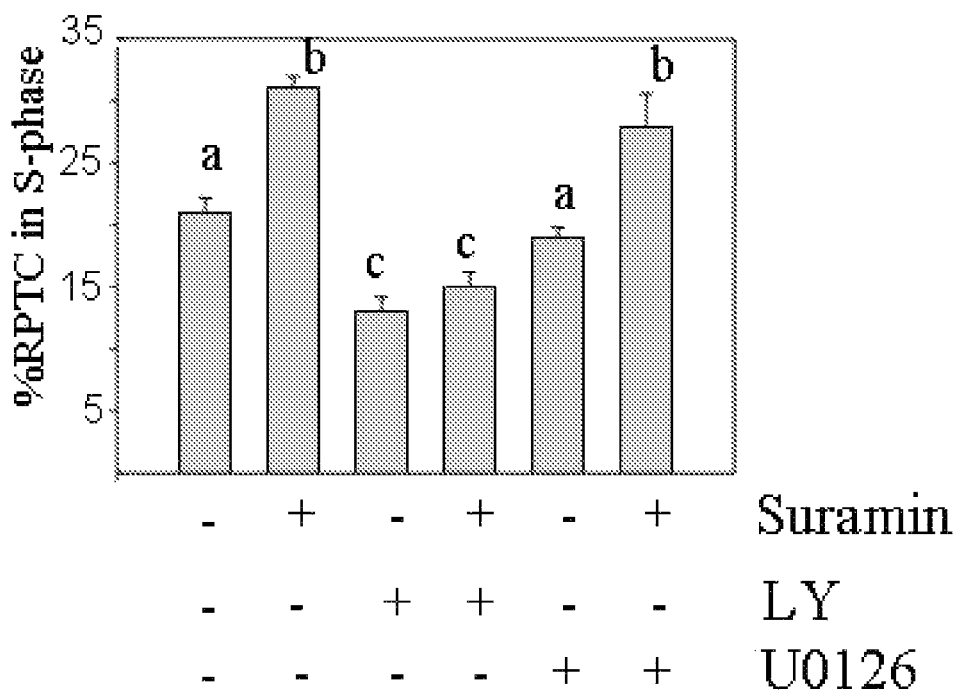
FIGS. 5B and 5C show RPTC cultured for 3 days and then incubated with 50 µM suramin for 24 hr in the presence and absence of 20 µM LY294002 (LY) and 10 µM U0126. Cell proliferation was determined by measuring the number of cells in S-phase of the cell cycle. Data are expressed as means+SEM, n=3. Bars with different superscripts are significantly from each other (p<0.05). Bright field photographs were taken at edges of the cell islands (40× magnification).

The two major factors that contribute to the movement of cells away from the edge of the explants are cell proliferation and migration (Boland et al., 1996). To investigate the effect of suramin on cell proliferation, we measured the number of cells in S-phase of the cell cycle. Approximately 20% of RPTC were in S-phase four days following plating and increased to 29% following a 24 hr suramin (50 µM) treatment (FIG. 1B). Incubation with exogenous EGF resulted in 32% of RPTC in S-phase. The combination of suramin and EGF did not significantly increase the number of RPTC in S-phase. Suramin concentrations lower than 50 µM did not statistically increase the number of RPTC in S-phase while 100 µM suramin did not further increase RPTC proliferation (FIG. 1C). Using the MTT assay, a 48 hr exposure of suramin also increased the number of RPTC by approximately 40% (FIG. 5A). Thus, suramin has the ability to induce RPTC proliferation.

Figure 2A:
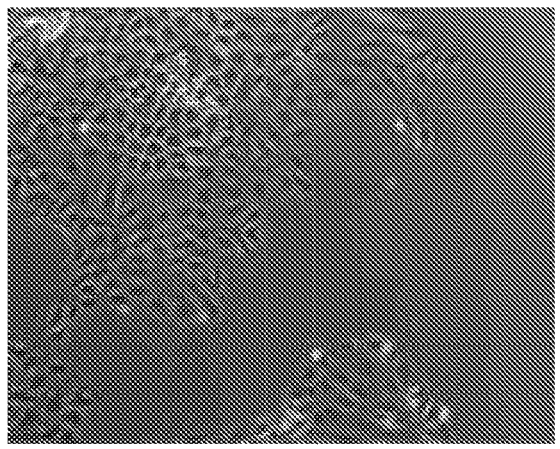
FIG. 2 shows suramin promotes RPTC scattering and formation of lamellipodia. RPTC were cultured for 3 days and then treated with diluent, 50 µM suramin, 10 ng/ml EGF or suramin+EGF. After 24 hr, bright field photographs were taken (40× magnification) (A) or RPTC were fixed with methanol and then stained with fluorescein conjugated phalloidin (B). Photographs at 80× magnification. Arrows show lamelliopodia.
Figure 2A:
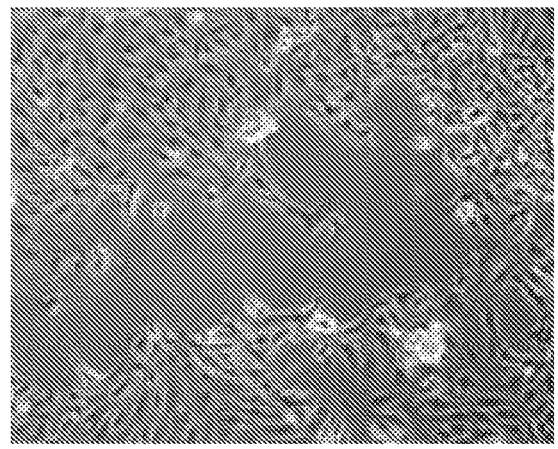
Figure 2A:
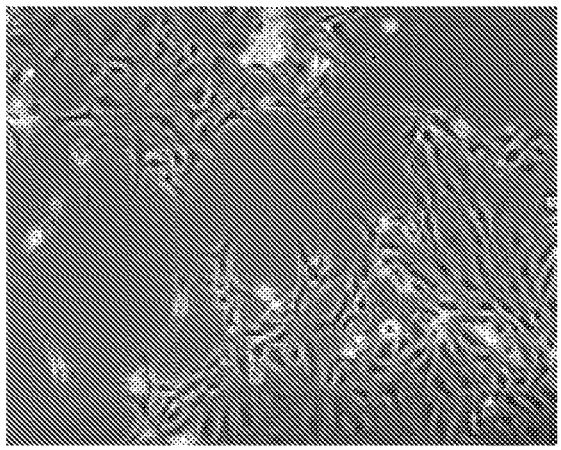
Figure 2A:
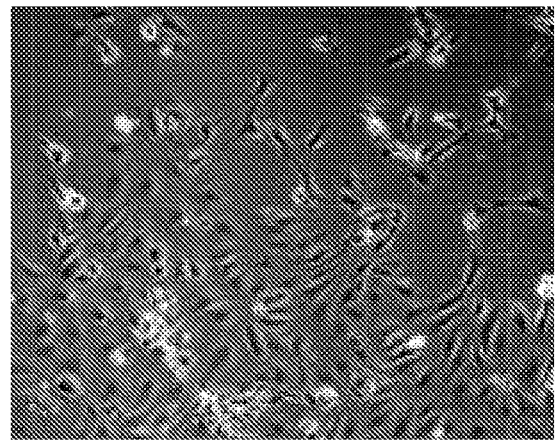

Motility requires the dissociation of some cells from cohesive epithelial sheets and their transformation into elongated, fibroblast-like cells (Casanova, 2002). As shown in FIG. 2A, most RPTC exhibited cobble stone morphology with few RPTC exhibiting fibroblast-like cell morphology during their growth. In response to suramin, RPTC at the edge of the cell island lost contact with their neighbors and became elongated, fibroblast-like cells. These morphological changes resemble RPTC at the edge of the cell island when treated with exogenous EGF.

Figure 2B:
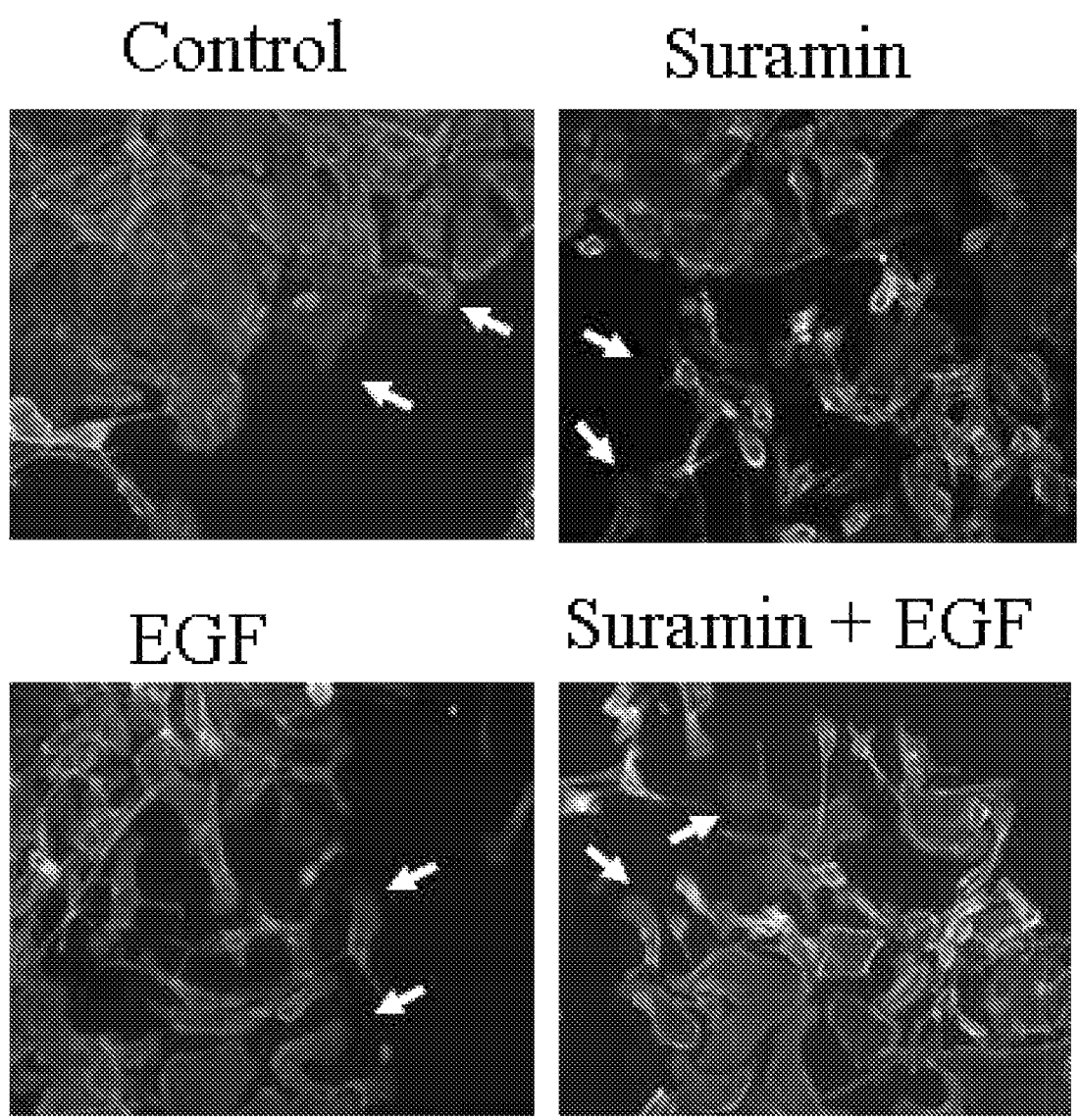

A prominent feature of migrating cells is formation of lamellipodia and the concomitant reorganization of the actin cytoskeleton (Fukata et al., 2003). Therefore, we examined the effect of suramin on RPTC scattering and motility using immunofluorescence staining of the actin cytoskeleton. Lamellipodia were seen at the edge RPTC in control cultures (FIG. 2B). Incubation of RPTC with suramin or EGF increased the formation of lamellipodia and decreased intercellular contacts, indicating cell scattering. Thus, RPTC scattering and motility increase following treatment with suramin and EGF.

Figure 3A:
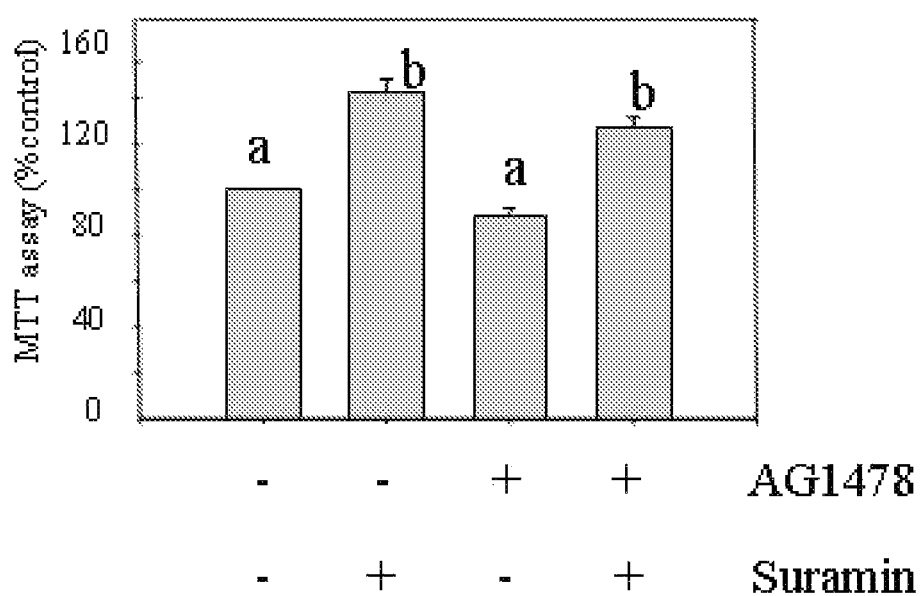
FIG. 3A shows RPTC cultured for 2 days and then incubated with 10 µM AG1478 in the absence or presence of 50 µM suramin for 48 hr. Cell proliferation was determined using the MTT assay. Data are expressed as means+SEM of the percentage of MTT activity compared to controls grown with diluent (N=3).
Figure 3B:
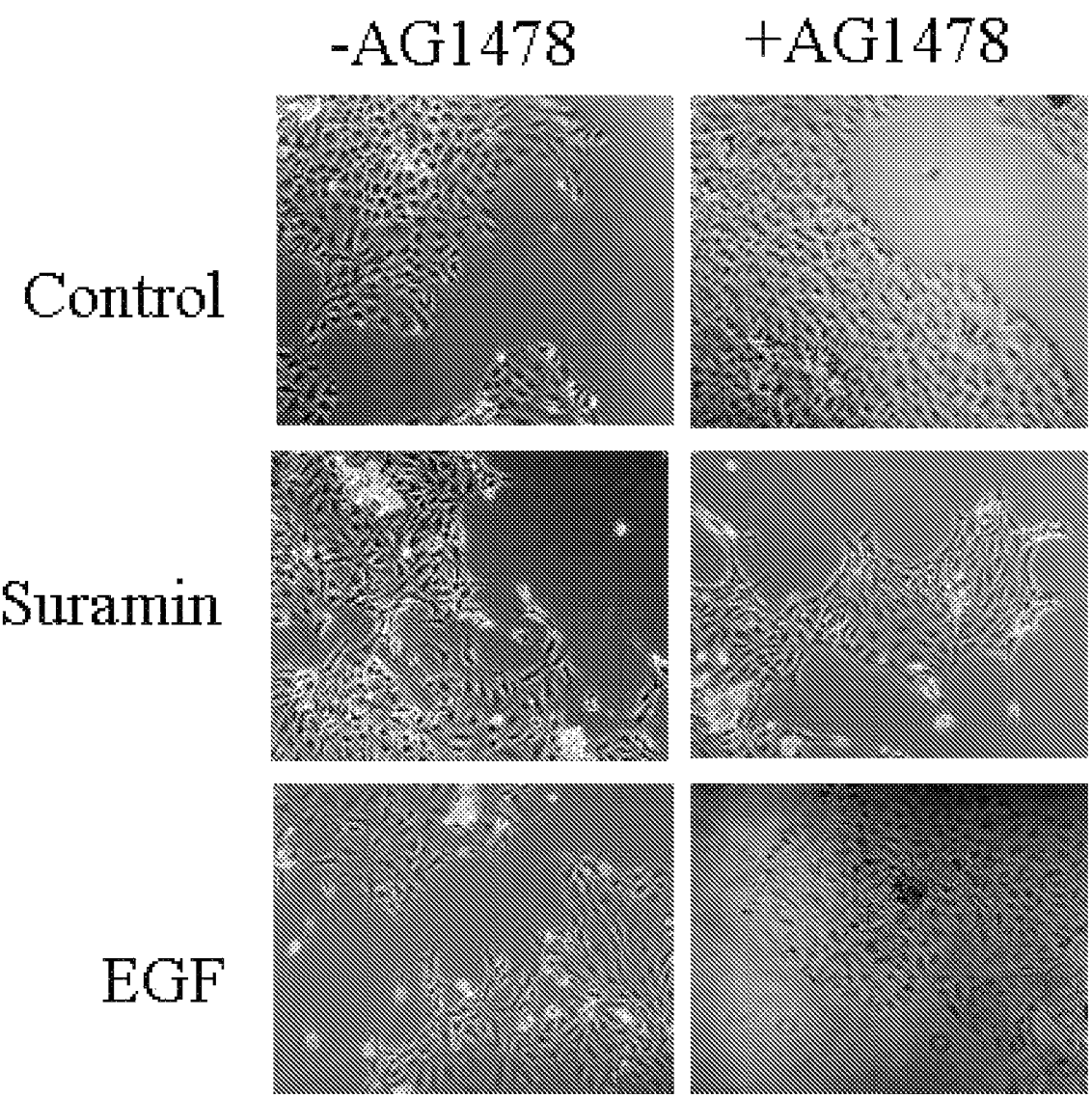
FIG. 3B shows RPTC cultured for 3 days and then incubated with diluent, 50 µM suramin, or 10 ng/ml EGF in the presence and absence of 10 µM AG1478 for 24 hr. Bright field photographs were taken at edge of the cell islands (40× magnification).

Suramin-induced RPTC proliferation and scattering are not mediated by the EGF receptor. Our previous studies showed that the EGF receptor is critical for RPTC proliferation (Zhuang et al., 2004). Because it was reported that suramin can induce the release of TGFα, an EGF receptor ligand, and stimulate proliferation in tumor cells (Cardinali et al., 1992), we examined the role of the EGF receptor in suramin-induced RPTC proliferation and scattering using AG1478, a selective EGF receptor inhibitor. AG1478 treatment did not affect suramin-induced RPTC proliferation as measured by MTT assay (FIG. 3A). Similarly, AG1478 did not affect suramin-induced formation of the fibroblast-like phenotype and scattering in RPTC (FIG. 3B). In contrast, AG1478 blocked EGF-induced formation of the fibroblast-like phenotype and scattering.

Figure 4A:
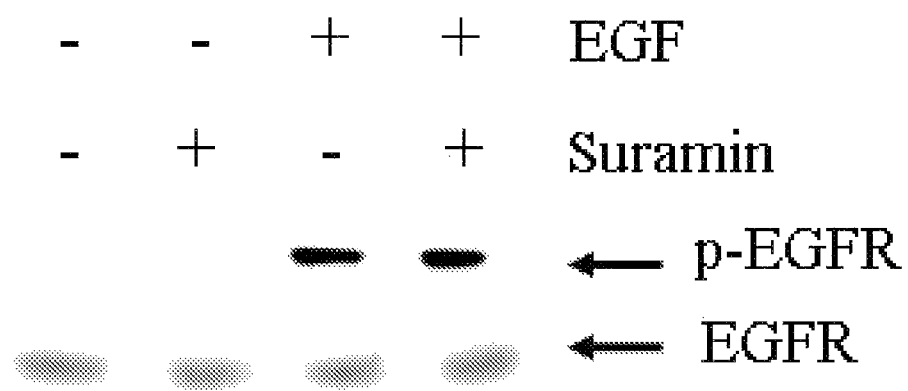
FIG. 4 shows suramin does not induce EGF receptor phosphorylation. RPTC were cultured for 3 days and then treated with 50 µM suramin or 10 ng/ml EGF for 10 min (A), or pretreated with 10 µM AG1478 for 1 hr and then exposed to EGF for 10 min (B). Cell lysates were prepared and subjected to immunoblot analysis using anti-phospho-EGF receptor antibody (Tyr1068) or anti-EGF receptor antibody. Protein loading was monitored using total EGF receptor levels. Representative immunoblot from three or more experiments.
Figure 4B:
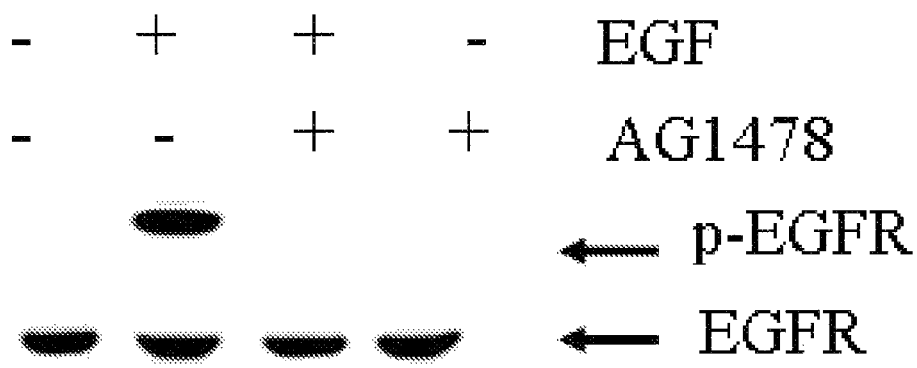

To determine whether suramin caused EGF receptor activation, we performed immunoblot analysis using an antibody against phosphorylated tyrosine 1068 of the EGF receptor. Total EGF receptor content was measured using immunoblot analysis and an antibody that recognizes the EGF receptor independent of its phosphorylation state to control for gel loading. We did not detect phosphorylated EGF receptor after treatment with suramin but did observe phosphorylated EGF receptor in response to exogenous EGF (FIG. 4A). The combination of suramin and EGF had no additional effect on EGF receptor phosphorylation. Further, AG 1478 inhibited EGF-induced EGF receptor phosphorylation (FIG. 4B). Thus, suramin induced RPTC proliferation and scattering is not through the EGF receptor.

Figure 5C:
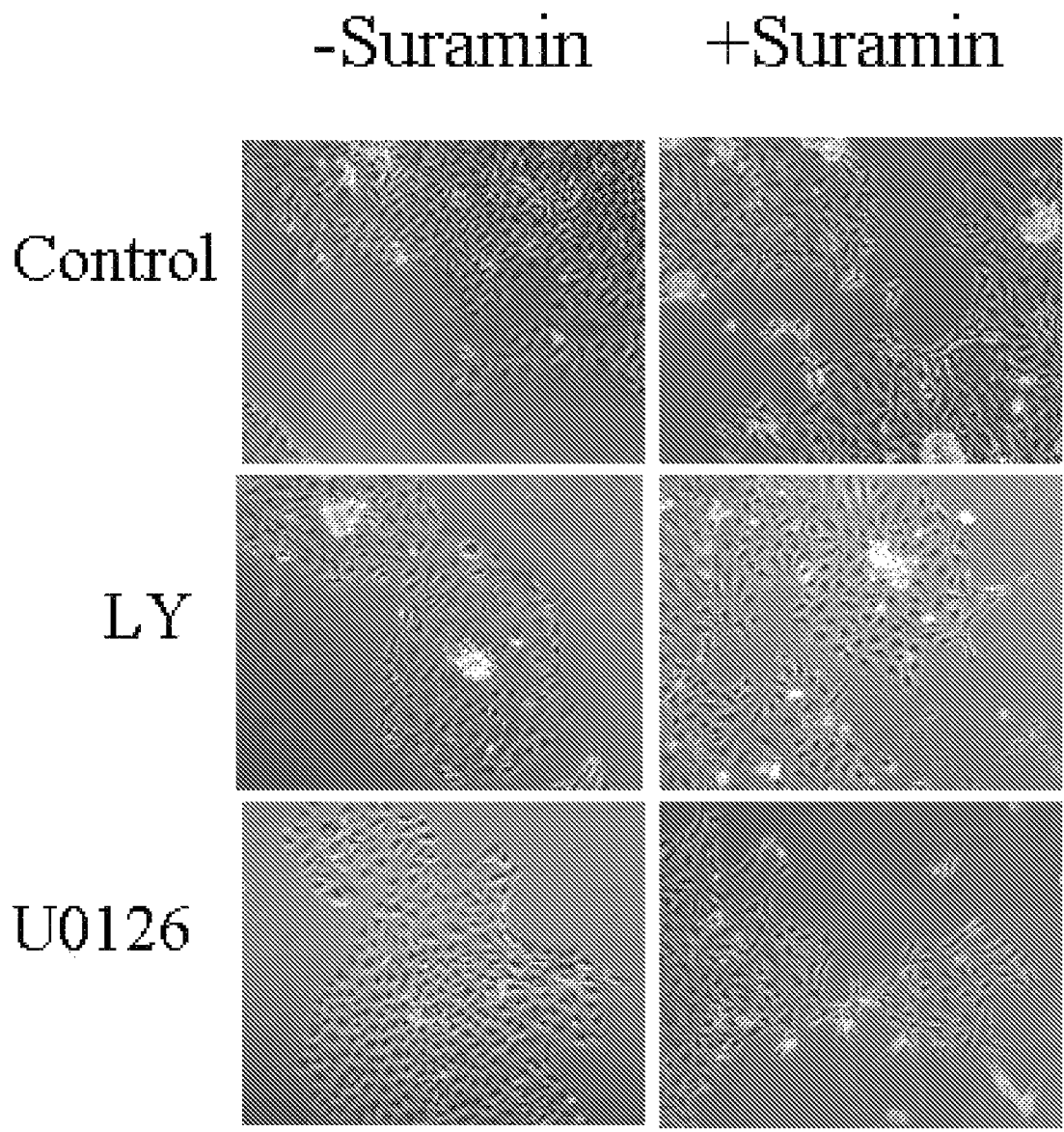

Activation of PI3K/Akt, but not ERK1/2, is required for suramin-induced RPTC proliferation and scattering. The PI3K/Akt and ERK1/2 pathways mediate cell proliferation and migration in different cell types and can be activated in response to different stimuli (Kyosseva, 2004; Richardson et al., 2004). In RPTC, PI3K/Akt, but not ERK1/2, mediates RPTC proliferation (Zhuang et al., 2004). To determine whether these two signaling pathways play a role in suramin-induced proliferation and scattering, RPTC were treated with the PI3K inhibitor LY294002 or the MEK inhibitor U0126 prior to suramin exposure. Inhibition of PI3K decreased suramin-induced proliferation while inhibition of MEK had no effect on proliferation, as measured by the MTT assay and the number of RPTC in S-phase of the cell cycle (FIGS. 5A and B). With respect to suramin-stimulated formation of fibroblast-like phenotype and RPTC scattering, LY294002 treatment partially inhibited them while U0126 had no effect (FIG. 5C).

Figure 6A:
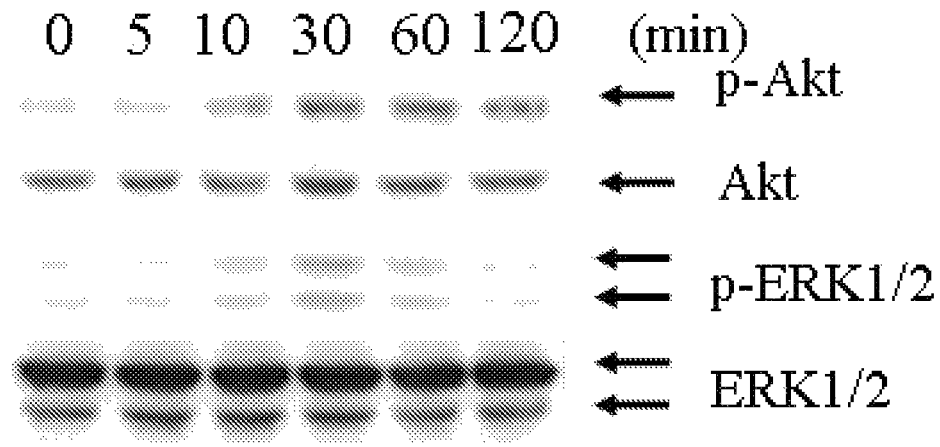
FIG. 6 shows suramin induces phosphorylation of Akt and ERK1/2. RPTC were cultured for 3 days and then treated with 50 μM suramin for 0-120 min (A) or pretreated with 20 μM LY294002 (LY)(B) or 10 μM U0126 (C) for 1 hr and exposed to suramin for 30 min. Cell lysates were prepared and subjected to immunoblot analysis using antibodies to phospho-Akt, phospho-ERK1/2, total Akt and total ERK1/2. Representative immunoblot from three or more experiments.

We evaluated whether the PI3K/Akt and/or ERK1/2 pathways are activated in RPTC in response to suramin. The activation of the PI3K and ERK1/2 pathways was measured using immunoblot analysis and antibodies that recognize phosphorylated Akt at serine 473 (a target of PI3K) and ERK1/2, respectively. Total Akt and ERK1/2 content was measured using immunoblot analysis and antibodies that recognize the Akt and ERK1/2 independent of their phosphorylation state to control for gel loading. Suramin-induced Akt phosphorylation within 10 min, reached a maximum at 30 min and was sustained through 120 min of treatment (FIG. 6A). ERK1/2 phosphorylation also was induced within 10 min and maximal at 30 min, but decreased to the control levels at 120 min.

Figure 6B:
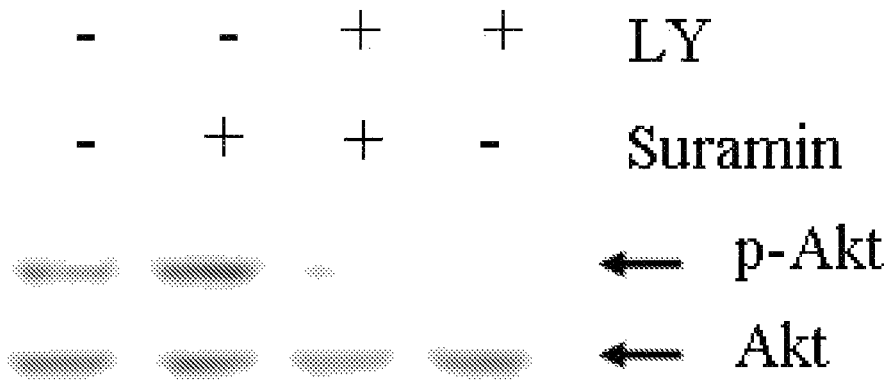
Figure 6C:
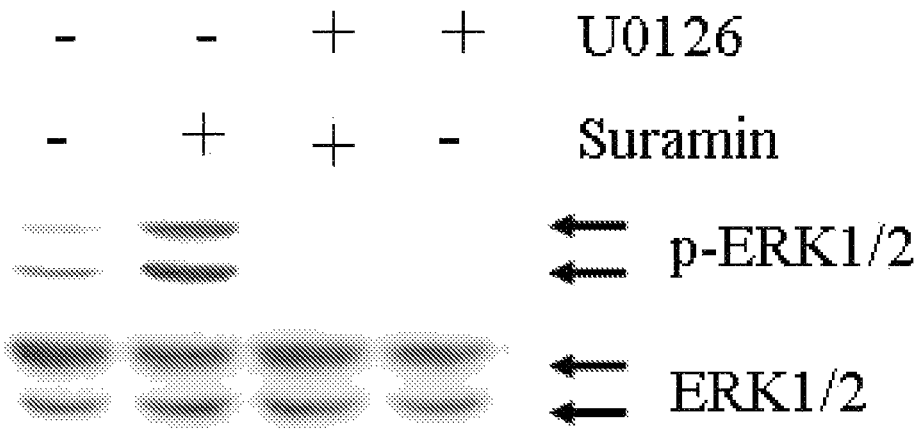

To confirm that LY294002 and U0126 selectively inhibited their respective kinases, we monitored Akt and ERK activation using immunoblot analysis and antibodies that recognized phosphorylated Akt and ERK1/2 as described above. LY294002 blocked Akt phosphorylation and U0126 blocked ERK1/2 phosphorylation of RPTC following plating in the presence and absence of suramin (FIGS. 6B and C). Thus, while PI3K/Akt and ERK1/2 are activated by suramin, PI3K/Akt, but not ERK1/2, is critical for suramin-induced RPTC proliferation and scattering. However, suramin-induced RPTC scattering is not completely dependent on PI3K.

Figure 7A:
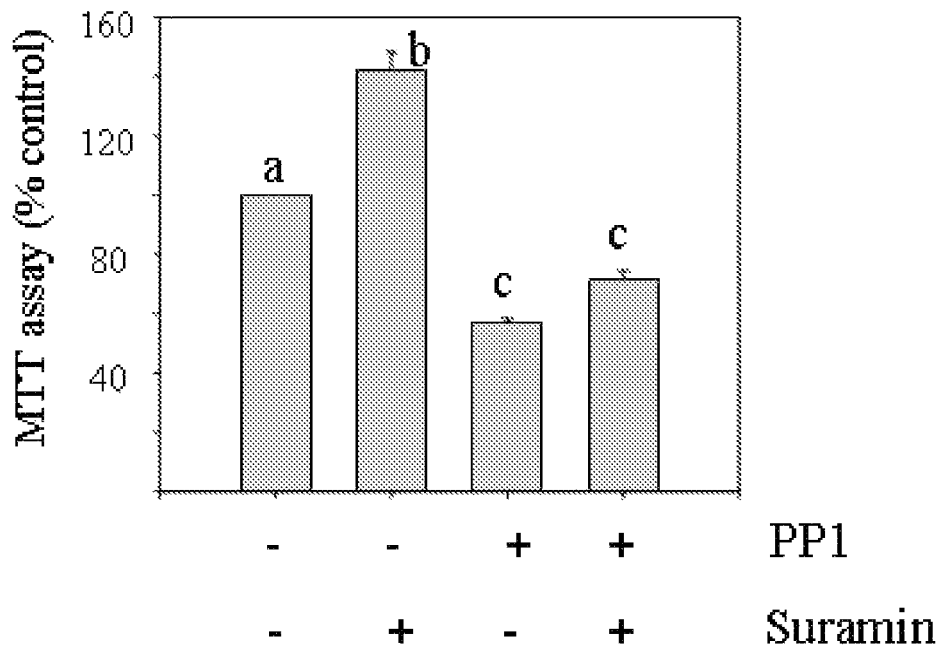
FIG. 7A shows RPTC cultured for 2 days and then incubated with 50 μM suramin for 48 hr in the presence and absence of 10 μM PP1. Cell proliferation was determined using the MTT assay. Data are expressed as means+SEM of the percentage of MTT activity compared to controls grown with diluent (N=3).
Figure 7B:
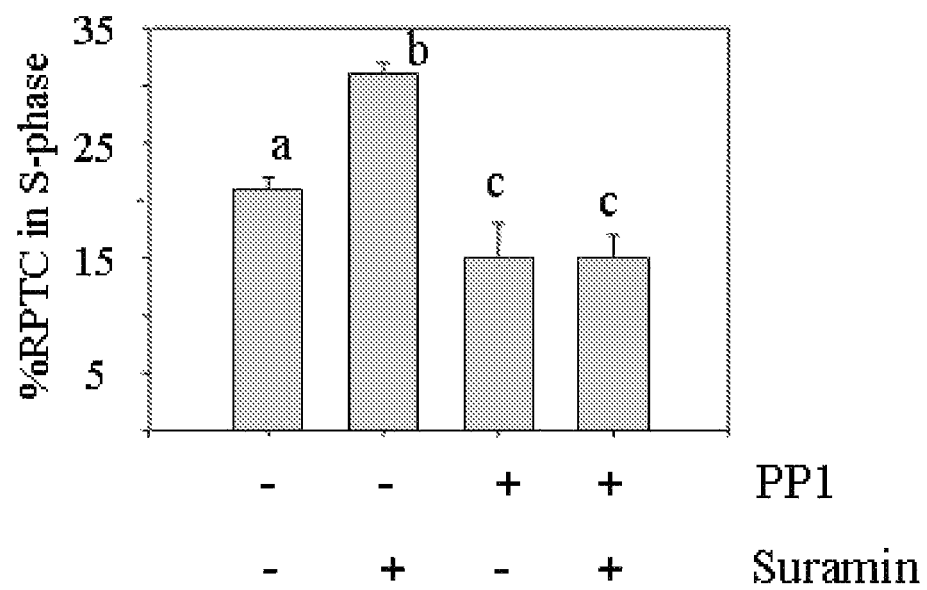
FIGS. 7B and 7C show RPTC cultured for 3 days and then incubated with 50 μM suramin for 24 hr in the presence and absence of 10 μM PP1. Cell proliferation was determined by measuring the number of cells in S-phase of the cell cycle. Data are expressed as means+SEM, n=3 Bars with different superscripts are significantly from each other (p<0.05). Bright field photographs were taken at edge of the cell islands (40× magnification).
Figure 7C:
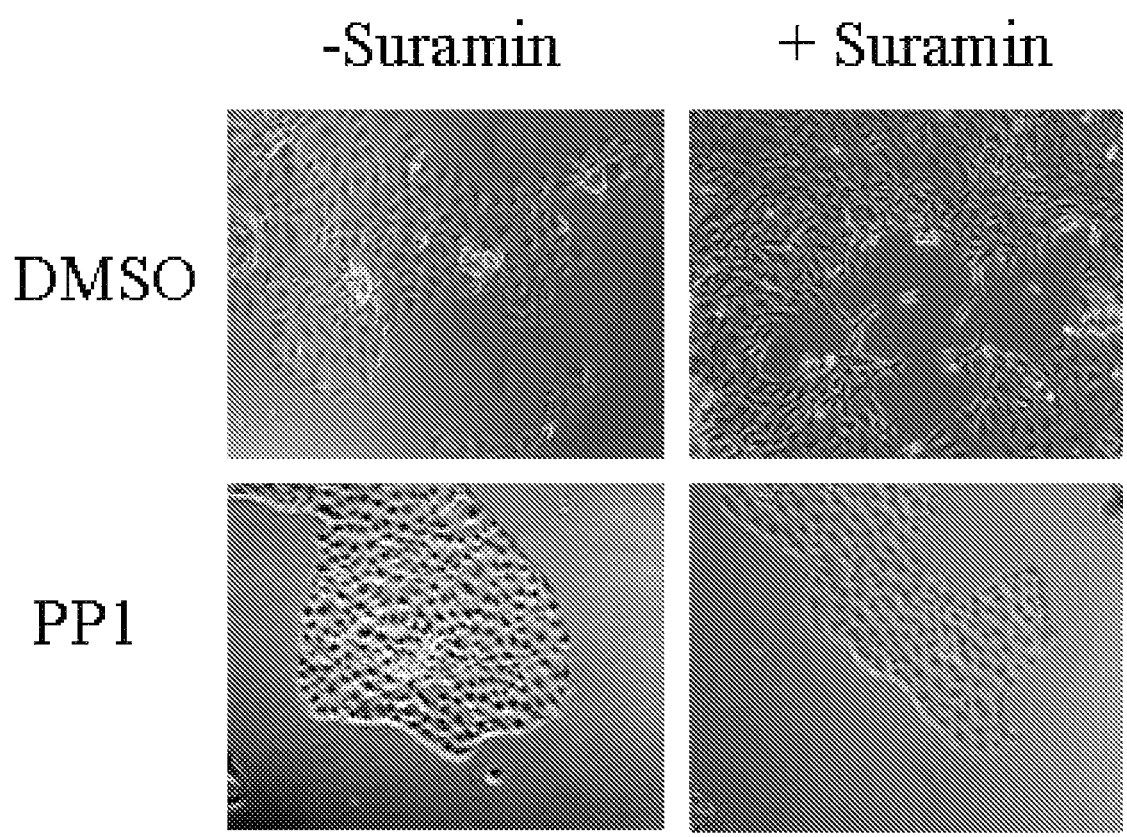

Src is required for RPTC proliferation and scattering induced by suramin. It has been reported that Src activation mediates proliferation of renal epithelial cells in response to arachidonic acid metabolites and that suramin can activate Src phosphorylation in keratinocytes (Chen et al., 1998; Brown et al., 2004). Thus, we examined whether Src is required for RPTC proliferation and scattering using PP1, a specific inhibitor of Src (Liu et al., 1999). Treatment of RPTC with PP1 inhibited RPTC proliferation in control and suramin-treated cells (FIGS. 7A and B). Also, suramin-stimulated formation of fibroblast-like phenotype and scattering in RPTC was blocked by PP1 (FIG. 7C).

Figure 8A:
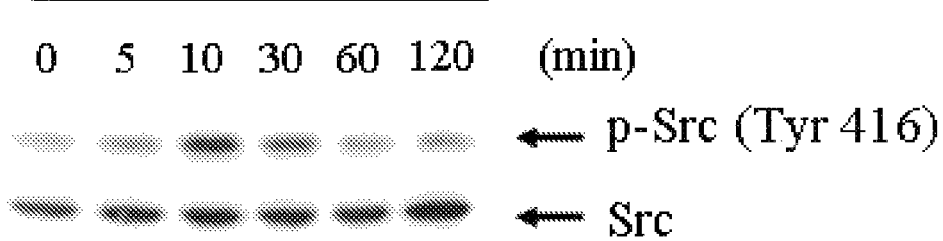
FIG. 8 shows Src, but not the EGF receptor, is required for suramin-induced Akt phosphorylation. RPTC were cultured for 3 days and then treated with 50 μM suramin for 0-60 min (A and B), or pretreated with 10 μM PP1 (C) and then treated with 50 μM suramin for 30 min. Cell lysates were prepared and subjected to immunoblot analysis using antibodies to phospho-Src at Tyr416 (A) and Tyr527 (B), Src, phospho-Akt, and total Akt. Representative immunoblot from three or more experiments.
Figure 8B:
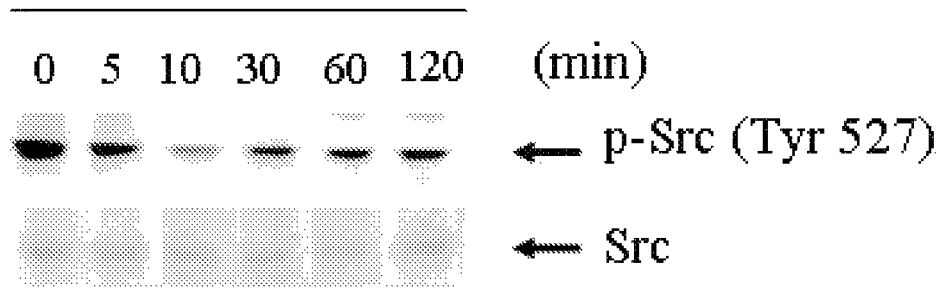
Figure 8C:
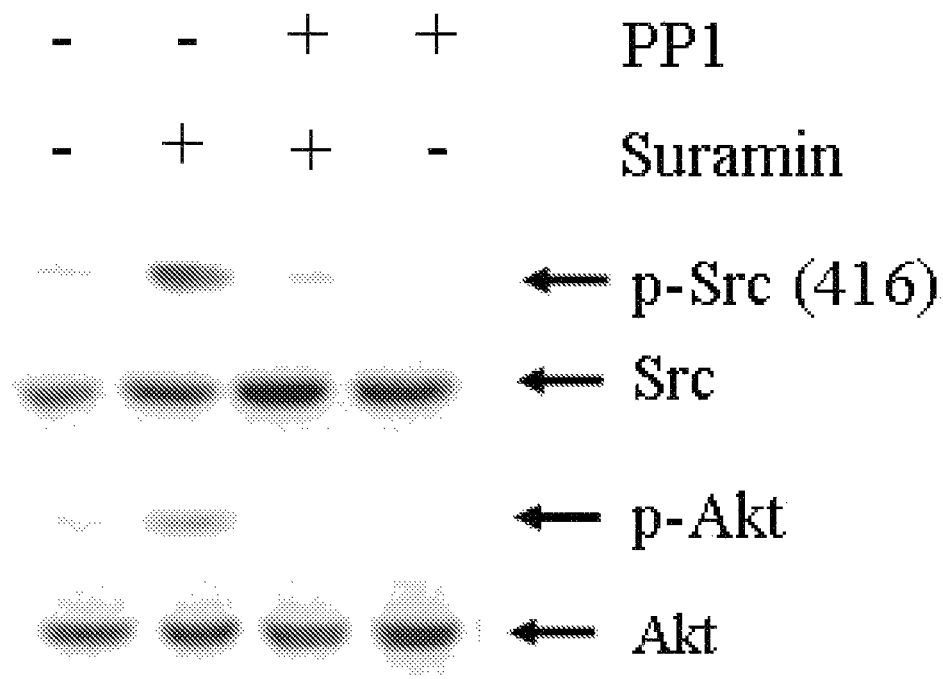

To determine whether suramin activates Src and whether Src mediates Akt activation, we examined the effect of suramin on Src phosphorylation and the effect of PP1 on suramin-induced Akt phosphorylation. Src activation requires dephosphorylation of tyrosine 527 (Zheng et al., 2000) and phosphorylation of tyrosine 416 in the catalytic domain (Leu and Maa, 2003). Src phosphorylation at tyrosine 416 was detected in control samples. Following suramin-treatment, Src phosphorylation increased within 10 min and returned to the basal level at 60 min (FIG. 8A). In contrast, suramin treatment reduced phosphorylation of Src at tyrosine 527 within 5 min and was sustained through 120 min (FIG. 8B). Pretreatment with PP1 blocked suramin-induced phosphorylation of Akt (FIG. 8C). Thus, suramin-induced RPTC proliferation and scattering is dependent on Src activity and Src is required for activation of the PI3K/Akt signaling pathway.

iv. Discussion

In this study, we found that suramin stimulates RPTC outgrowth, scattering and proliferation. Consistent with our observations, the stimulatory effect of suramin on cell proliferation has been reported in several tumor cell lines including breast cancer cells (Foekens et al., 1992), non-small-cell lung cancer cell lines (Lokshin et al., 1999), esophageal and epidermoid carcinoma cell lines (Cardinali et al., 1992), as well as both PC12 cells and dorsal root ganglion neurons (Gill et al., 1996). Thus, in addition to its antiproliferative activity in some models, suramin induces cellular proliferation in certain cell types. Further, the effect of suramin on formation of motile RPTC phenotype and scattering suggests that it is also a stimulator of RPTC migration. Our results are different from a previous report that showed that suramin inhibits [3H]thymidine uptake induced by conditioned media in an injured renal epithelial cell line (LLC-PK1) (Anderson and Ray, 1998). The reasons for the difference of these two observations are currently unknown, it may be due to different cell types and models being used.

The mechanisms underlying suramin stimulation of cell proliferation and scattering are not clear. Since an early study showed that suramin induces the release of TGFβ, a EGF receptor ligand, activates the EGF receptor, and induces proliferation of the carcinoma cell line KEsC-II (Cardinali et al., 1992), we initially thought that an EGF receptor mediated mechanism may account for RPTC proliferation and scattering. However, our data do not support this hypothesis. First, suramin did not induce phosphorylation of the EGF receptor. Second, suramin did not affect exogenous EGF-induced EGF receptor phosphorylation. Finally, treatment of cells with AG1478, a specific EGF receptor inhibitor, did not affect suramin-induced phosphorylation of Akt, proliferation or scattering. Consistent with our observation, inhibition of the EGF receptor with AG1478 did not attenuate suramin-induced ERK activation and proliferation in Chinese hamster ovary cells (Nakata, 2004). While it is possible that suramin may stimulate activation of other growth factor receptors through ligand-dependent mechanism, and PDGF and FGF receptors are found on RPTC, the ligands for these receptors are not expressed in RPTC (Toback, 1992). Thus, we conclude that suramin-stimulated RPTC proliferation and scattering are not through the production of autocrine growth factors.

Another potential mechanism for suramin-induced RPTC proliferation and scattering may involve interference with growth inhibitory factors. In this regarding, it has been reported that suramin is able to block the interaction of TGFβ with the TGF receptor and block the inhibitory effect of TGFβ in renal cancer cells (Wade et al., 1992). Previous results from our laboratory showed that RPTC can produce TGFβ and that oxidant-induced autocrine production of TGFβ has an inhibitory effect on RPTC proliferation (Nowak and Schnellmann, 1997). Further, addition of exogenous TGFβ to RPTC inhibited proliferation following plating and oxidant injury (Counts et al., 1995; Kays et al., 1996; Nowak and Schnellmann, 1997) and inhibited wounding healing of renal epithelial cells following mechanical injury (Sponsel et al., 1994). Thus, it is possible that inhibition of TGFβ binding to its receptor may result in enhancement of RPTC proliferation and scattering after suramin treatment. This possibility is currently under investigation in our laboratory.

Our results revealed that Src is a mediator of suramin-induced proliferation and scattering of RPTC. Evidence for this statement is the activation of Src and Akt by suramin, the inhibition of suramin-induced Src and Akt phosphorylation by the Src inhibitor PP1, and the inhibition of RPTC proliferation and scattering by PP1. The mechanism by which suramin induces Src activation is currently unclear. One possibility is that suramin induces activation of protein tyrosine phosphatases (PTPs) and, as a result, Src is activated. Previous studies have shown that Src activation results from dephosphorylation of Tyr-527 and subsequent Src autophosphorylation of Tyr-416 (Roskoski, 2004) and PTPα has been reported to positively regulate Src activity via dephosphorylating Src at tyrosine 527 (Harder et al., 1998; Zheng et al., 2000). Further, suramin induces activation of PTPα in vitro (McCain et al., 2004). Alternatively, suramin may induce Src activation by blocking TGFβ binding to its receptor. In this context, it has been reported that TGFβ treatment decreases Src activity and cell growth in prostate carcinoma cell line PC3 and hepatoma cell line HepG2 (Atfi et al., 1994; Fukuda et al., 1998), and prevents hepatocyte growth factor-induced tyrosine phosphorylation of Src and migration in endothelial cells (Manganini and Maier, 2000).

To identify the intracellular signaling mechanism responsible for suramin-induced proliferation and scattering of RPTC, we found that Akt, a downstream target of PI3K is phosphorylated after suramin treatment and LY 294002, a specific inhibitor of PI3K signaling pathway attenuated proliferation and scattering. These data illustrate that PI3K plays an essential role in transducing the signal for RPTC proliferation and scattering in response to suramin stimulation. However, it should be noted that PI3K/Akt signaling pathway may not be the sole pathway responsible for RPTC scattering because blockade of PI3K does not result in complete inhibition on RPTC scattering in response to suramin stimulation. Although suramin also induced phosphorylation of ERK1/2, inhibition of this signaling pathway did not affect either proliferation or scattering, suggesting that ERK pathway does not mediate these suramin-induced biological process.

In summary, our studies have demonstrated that suramin stimulates proliferation and scattering of RPTC, which was mediated by Src dependent activation of PI3K/Akt pathway. Further, suramin stimulated biological responses do not involve EGF receptor or ERK1/2 activation. Since proliferation and migration of renal epithelial cells are two crucial processes needed for structural regeneration of nephron following injury, it will be of interest to determine whether suramin has a therapeutic potential in promoting renal recovery after injury.

2. Example 2

In Vivo Repair and Regeneration

Experiments were designed to investigate whether suramin stimulated recovery of renal function in a mouse renal ischemic/reperfusion (I/R) acute renal failure model. Male C57BL/6 mice weighing 25-30 g were subjected to I/R injury using bilateral renal artery clamping for 26 min and then allowed to recover over time. The renal pedicles were isolated, but no clamps were applied in the sham group. Some mice subjected to I/R were treated with a single intravenous dose of suramin (0.001-10 mg/kg) or diluent 24 hr after reperfusion. Blood was collected at 24 and 48 hr after injury and serum creatinine levels measured as a marker of acute renal failure.

Figure 9:
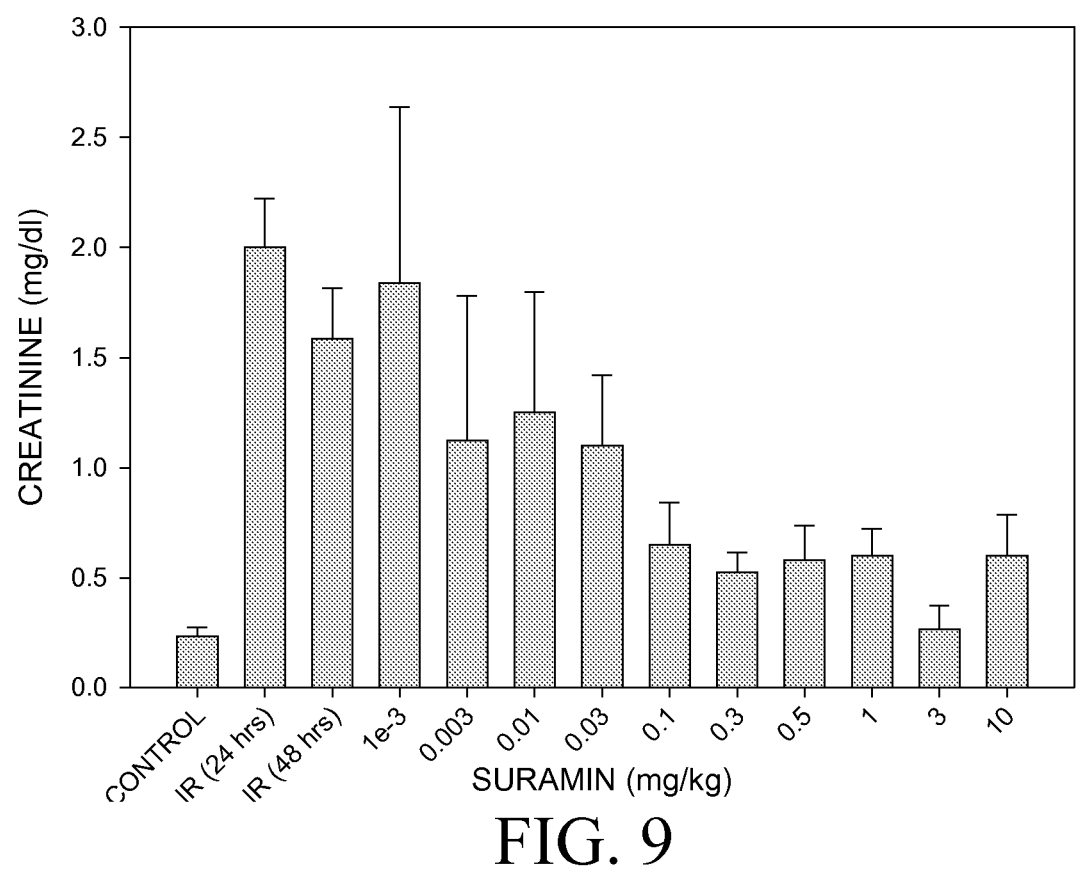
FIG. 9 shows serum creatinine levels increased at 24 hrs post reperfusion to approximately 2 mg/dl and remained at this level at 48 hrs in mice subjected to ischemia/reperfusion (I/R) and diluent. Suramin, added 24 hr after I/R, at doses between 0.003 and 0.03 mg/kg stimulated recovery of renal function and decreased serum creatinine levels to approximately 1 mg/dl. Doses of suramin greater than or equal to 0.1 mg/dl completely restored renal function. Finally no toxicity was observed at doses of suramin up to 10 mg/kg.

Serum creatinine levels increased at 24 hrs post reperfusion to approximately 2 mg/dl and remained at this level at 48 hrs in mice subjected to I/R and diluent. Suramin doses between 0.003 and 0.03 mg/kg stimulated recovery of renal function decreased serum creatinine levels to approximately 1 mg/dl. Doses of suramin greater than or equal to 0.1 mg/dl completely restored renal function. Finally no toxicity was observed at doses of suramin up to 10 mg/kg. See FIG. 9.

In a mouse model of ischemia/reperfusion-induced acute renal failure, we demonstrate that suramin, given after acute renal failure is fully established, can stimulate complete recovery of renal function at low doses (0.1 mg/kg) and does not cause toxicity at doses 100 times greater.

J. References

Anderson R J and Ray C J (1998) Potential autocrine and paracrine mechanisms of recovery from mechanical injury of renal tubular epithelial cells. Am J Physiol 274:F463-472.

Atfi A, Drobetsky E, Boissonneault M, Chapdelaine A and Chevalier S (1994) Transforming growth factor beta down-regulates Src family protein tyrosine kinase signaling pathways. J Biol Chem 269:30688-30693.

Barrett M P, Burchmore R J, Stich A, Lazzari J O, Frasch A C, Cazzulo J J and Krishna S (2003) The trypanosomiases. Lancet 362:1469-1480.

Betsholtz C, Johnsson A, Heldin C H and Westermark B (1986) Efficient reversion of simian sarcoma virus-transformation and inhibition of growth factor-induced mitogenesis by suramin. Proc Natl Acad Sci USA 83:6440-6444.

Boland S, Boisvieux-Ulrich E, Houcine O, Baeza-Squiban A, Pouchelet M, Schoevaert D and Marano F (1996) TGF beta 1 promotes actin cytoskeleton reorganization and migratory phenotype in epithelial tracheal cells in primary culture. J Cell Sci 109:2207-2219.

Braddock, P S., Hu D E, Fan, T P., Stratford, I J., Harris, A L., and Bicknell, R. (1994). A structure-activity analysis of antagonism of the growth factor and angiogenic activity of basic fibroblast growth factor by suramin and related polyanions. British Journal of Cancer 69, 890-8 (incorporated herein by reference for its teaching of a suramin derivative).

Brown T A, Yang T M, Zaitsevskaia T, Xia Y, Dunn C A, Sigle R O, Knudsen B and Carter W G (2004) Adhesion or plasmin regulates tyrosine phosphorylation of a novel membrane glycoprotein p80/gp140/CUB domain-containing protein 1 in epithelia. J Biol Chem 279:14772-14783.

Cardinali M, Sartor O and Robbins K C (1992) Suramin, an experimental chemotherapeutic drug, activates the receptor for epidermal growth factor and promotes growth of certain malignant cells. J Clin Invest 89:1242-1247.

Casanova J E (2002) Epithelial cell cytoskeleton and intracellular trafficking V. Confluence of membrane trafficking and motility in epithelial cell models. Am J Physiol Gastrointest Liver Physiol 283:G1015-1019.

Chen J K, Falck J R, Reddy K M, Capdevila J and Harris R C (1998) Epoxyeicosatrienoic acids and their sulfonimide derivatives stimulate tyrosine phosphorylation and induce mitogenesis in renal epithelial cells. J Biol Chem 273: 29254-29261.

Coffey R J, Jr., Leof E B, Shipley G D and Moses H L (1987) Suramin inhibition of growth factor receptor binding and mitogenicity in AKR-2B cells. J Cell Physiol 132:143-148.

Counts R S, Nowak G, Wyatt R D and Schnellmann R G (1995) Nephrotoxicant inhibition of renal proximal tubule cell regeneration. Am J Physiol 269:F274-281.

Dhar, S., Gullbo, J., Csoka, K., Eriksson, E., Nilsson, K., Nickel, P., Larsson, R., and Nygren, P. (2000). Antitumor activity of suramin analogues in human tumour cell lines and primary cultures of tumour cells from patients. European Journal of Cancer 36, 803-809 (incorporated herein by reference for its teaching of a suramin derivative).

Eisenberger M A and Reyno L M (1994) Suramin. Cancer Treat Rev 20:259-273.

Firsching, A., Nickel, P., Mora, P., and Allolio, Bruno. (1995). Antiproliferative and angiostatic activity of suramin analogues. Cancer Research 55, 4957-4961 (incorporated herein by reference for its teaching of a suramin derivative).

Foekens J A, Sieuwerts A M, Stuurman-Smeets E M, Dorssers L C, Berns E M and Klijn J G (1992) Pleiotropic actions of suramin on the proliferation of human breast-cancer cells in vitro. Int J Cancer 51:439-444.

Fukata M, Nakagawa M and Kaibuchi K (2003) Roles of Rho-family GTPases in cell polarisation and directional migration. Curr Opin Cell Biol 15:590-597.

Fukuda K, Kawata S, Tamura S, Matsuda Y, Inui Y, Igura T, Inoue S, Kudara T and Matsuzawa Y (1998) Altered regulation of Src tyrosine kinase by transforming growth factor beta1 in a human hepatoma cell line. Hepatology 28:796-804.

Gagliardi, A. R. T., Kassack, M., Kreimeyer, A., Muller, G., Nickel, P., and Collins, D. C. (1998). Antiangiogenic and antiproliferative activity of suramin analogues. Cancer Chemother Pharmacol 41, 117-124 (incorporated herein by reference for its teaching of a suramin derivative).

Gill J S, Connolly D C, McManus M J, Maihle N J and Windebank A J (1996) Suramin induces phosphorylation of the high-affinity nerve growth factor receptor in PC12 cells and dorsal root ganglion neurons. J Neurochem 66:963-972.

Harder K W, Moller N P, Peacock J W and Jirik F R (1998) Protein-tyrosine phosphatase alpha regulates Src family kinases and alters cell-substratum adhesion. J Biol Chem 273:31890-31900.

Herbst R S (2004) Review of epidermal growth factor receptor biology. Int J Radiat Oncol Biol Phys 59:21-26.

Hosang M (1985) Suramin binds to platelet-derived growth factor and inhibits its biological activity. J Cell Biochem 29:265-273.

Kaur M, Reed E, Sartor O, Dahut W and Figg W D (2002) Suramin's development: what did we learn? Invest New Drugs 20:209-219.

Kays S E, Nowak G and Schnellmann R G (1996) Transforming growth factor-beta 1 inhibits regeneration of renal proximal tubular cells after oxidant exposure. J Biochem Toxicol 11:79-84.

Konety B R and Getzenberg R H (1997) Novel therapies for advanced prostate cancer. Semin Urol Oncol 15:33-42.

Kooistra A, Romijn J C and Schroder F H (1997) Stromal inhibition of epithelial cell growth in the prostate; overview of an experimental study. Urol Res 25:S97-105.

Kreimeyer, A., Muller, G., Kassack, M., Nickel. P., and Gagliardi, A. R. T. (1998). Sulfanilic Acid-, benzenedisulfonic acid-, and naphthalenetrisulfonic acid analogues. Arch. Pharm. Pharm. Med. Chem. 331, 97-103 (incorporated herein by reference for its teaching of a suramin derivative).

Kyosseva S V (2004) Mitogen-activated protein kinase signaling. Int Rev Neurobiol 59:201-220.

Leu T H and Maa M C (2003) Functional implication of the interaction between EGF receptor and c-Src. Front Biosci 1:s28-38.

Liu Y, Bishop A, Witucki L, Kraybill B, Shimizu E, Tsien J, Ubersax J, Blethrow J, Morgan D O and Shokat K M (1999) Structural basis for selective inhibition of Src family kinases by PP1. Chem Biol 6:671-678.

Lokshin A, Peng X, Campbell P G, Barsouk A and Levitt M L (1999) Mechanisms of growth stimulation by suramin in non-small-cell lung cancer cell lines. Cancer Chemother Pharmacol 43:341-347.

Maeshima A, Nojima Y and Kojima I (2002) Activin A: an autocrine regulator of cell growth and differentiation in renal proximal tubular cells. Kidney Int 62:446-454.

Manganini M and Maier J A (2000) Transforming growth factor beta2 inhibition of hepatocyte growth factor-induced endothelial proliferation and migration. Oncogene 19:124-133.

Marchetti, D., Reiland, J., Erwin, B., and Roy., M. (2003). Inhibition of heparanase activity and heparanase-induced angiogenesis by suramin analogues. Int. J. Cancer 104, 167-174 (incorporated herein by reference for its teaching of a suramin derivative).

McCain D F, Wu L, Nickel P, Kassack M U, Kreimeyer A, Gagliardi A, Collins D C and Zhang Z Y (2004) Suramin derivatives as inhibitors and activators of protein-tyrosine phosphatases. J Biol Chem 279:14713-14725.

McCain, D. F., Wu, L., Nickel, P., Kassack, U., Kreimeyer, A., Gagliardi, A., Collins, D. C., and Zhang, Z. Y. (2004). Suramin derivatives as inhibitors and activators of protein-tyrosine phosphatases. J. Biol. Chem. 279, 14713-14725 (incorporated herein by reference for its teaching of a suramin derivative).

Meyers, M. O., Gagliardi, A. R., Flattmann, G. J., Su, J. L., Wang, Y. Z., and Woltering, E. A. (2000) Suramin analogs inhibit human angiogenesis in vitro. J. Surg. Res. 91, 130-134 (incorporated herein by reference for its teaching of a suramin derivative).

Nakata H (2004) Stimulation of extracellular signal-regulated kinase pathway by suramin with concomitant activation of DNA synthesis in cultured cells. J Pharmacol Exp Ther 308:744-753.

Nowak G and Schnellmann R G (1995) Improved culture conditions stimulate gluconeogenesis in primary cultures of renal proximal tubule cells. Am J Physiol 268:C1053-1061.

Nowak G and Schnellmann R G (1996) L-ascorbic acid regulates growth and metabolism of renal cells: improvements in cell culture. Am J Physiol 271:C2072-2080.

Nowak G and Schnellmann R G (1997) Renal cell regeneration following oxidant exposure: inhibition by TGF-beta1 and stimulation by ascorbic acid. Toxicol Appl Pharmacol 145:175-183.

Richardson C J, Schalm S S and Blenis J (2004) PI3-kinase and TOR: PIKTORing cell growth. Semin Cell Dev Biol 15:147-159.

Rodeheaver D P, Alco M D and Schnellmann R G (1990) Differences in enzymatic and mechanical isolated rabbit renal proximal tubules: comparison in long-term incubation. In Vitro Cell Dev Biol 26:898-904.

Roskoski R, Jr. (2004) Src protein-tyrosine kinase structure and regulation. Biochem Biophys Res Commun 324:1155-1164.

Sponsel H T, Breckon R, Hammond W and Anderson R J (1994) Mechanisms of recovery from mechanical injury of renal tubular epithelial cells. Am J Physiol 267:F257-264.

Stein C A (1993) Suramin: a novel antineoplastic agent with multiple potential mechanisms of action. Cancer Res 53:2239-2248.

Toback F G (1992) Regeneration after acute tubular necrosis. Kidney Int 41:226-246.

Wade T P, Kasid A, Stein C A, LaRocca R V, Sargent E R, Gomella L G, Myers C E and Linehan W M (1992) Suramin interference with transforming growth factor-beta inhibition of human renal cell carcinoma in culture. J Surg Res 53:195-198.

Wang J Y and Williams L T (1984) A v-sis oncogene protein produced in bacteria competes for platelet-derived growth factor binding to its receptor. J Biol Chem 259:10645-10648.

Zheng X M, Resnick R J and Shalloway D (2000) A phosphotyrosine displacement mechanism for activation of Src by PTPalpha. Embo J 19:964-978.

Zhuang S, Dang Y and Schnellmann R G (2004) Requirement of the epidermal growth factor receptor in renal epithelial cell proliferation and migration. Am J Physiol Renal Physiol 287:F365-F372.

What is claimed is:

1. A method of promoting tissue repair and/or regeneration in a subject, comprising administering to a subject in need of tissue repair and/or regeneration a composition comprising a therapeutically effective amount of a compound comprising the structure:

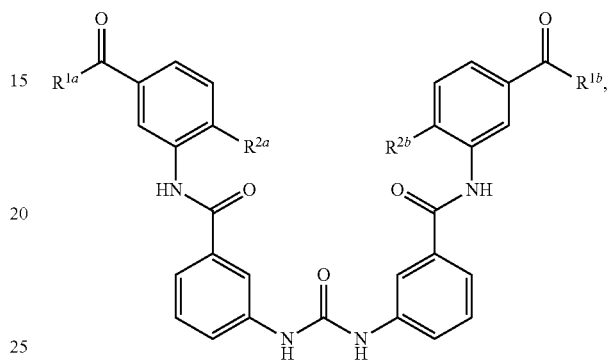

wherein $R^{1a}$ and $R^{1b}$ are, independently, hydrogen, hydroxyl, alkyl, aryl, alkoxy, carboxyl, ester, ester, amino, amide, substituted naphthalene, aniline or phenyl, and wherein $R^{2a}$ and $R^{2b}$ are, independently, hydrogen, hydroxyl, alkyl, aryl, acyl, alkoxy, carboxyl, ester, amino, amide, or halide, wherein the subject has been diagnosed with a renal ischemic injury and wherein the compound is administered parenterally at a dosage of between 0.001 and about 3 mg/kg body weight.

2. The method of claim 1, wherein the substituted naphthalene, aniline or phenyl is selected from the group consisting of aminonaphthalene-4,6,8-trisulfonic acid, aminonaphthalene-3,6,8-trisulfonic acid, aniline-3-sulfonic acid, aninline-4-sulfonic acid, aniline-2,4-disulfonic acid, aniline-2,5-disulfonic acid, aninline-3-phosphonic acid, aniline-4-phosphonic acid, 4-methylaniline-3-phosphonic acid, and phenyl sulfonic acid.

3. The method of claim 1, wherein the composition is administered at least 24 hours after the renal ischemic injury.

4. The method of claim 1, wherein the tissue does not comprise a cancer or tumor.

5. The method of claim 1, wherein the composition comprises suramin.

6. The method of claim 5, wherein the suramin is administered at a dose from about 0.01 to about 3 mg/kg.

7. The method of claim 6, wherein the suramin is administered at a dose of from about 0.3 to about 3 mg/kg.

8. The method of claim 6, wherein the suramin is administered at a dose of about 0.1 mg/kg.

* * * * *

UNITED STATES PATENT AND TRADEMARK OFFICE
CERTIFICATE OF CORRECTION

PATENT NO. : 8,633,250 B2
APPLICATION NO. : 11/622285
DATED : January 21, 2014
INVENTOR(S) : Rick G. Schnellmann et al.

It is certified that error appears in the above-identified patent and that said Letters Patent is hereby corrected as shown below:

On title page, item (54), delete "CELL REPAIR AND REGENERATION BY SURAMIN AND RELATED POLYSULFONATED NAPTHYLUREAS" and replace with --CELL REPAIR AND REGENERATION BY SURAMIN AND RELATED POLYSULFONATED NAPHTHYLUREAS-- therefor.

On title page, item (56) References Cited - Other Publications, delete the 9th reference on page 1 "Atfi A, Drobetsky E, Boissonneault M, Chapdelaine a and Chevalier S (1994) Transforming growth factor beta down-regulates Src family protein tyrosine kinase signaling pathways. J Biol Chem 269:30688-30693." and replace with --Atfi A, Drobetsky E, Boissonneault M, Chapdelaine A and Chevalier S (1994) Transforming growth factor beta down-regulates Src family protein tyrosine kinase signaling pathways. J Biol Chem 269:30688-30693.-- therefor.

On title page, item (56) References Cited - Other Publications, delete the 17th reference on page 2 "Gill JS Connolly DC, McManus MJ, Maihle NJ and Windebank AJ (1996) Suramin induces phosphorylation of the high-affinity nerve growth factor receptor in PC12 cells and dorsal root ganglion neurons. J Neurochem 66:963-972." and replace with --Gill JS, Connolly DC, McManus MJ, Maihle NJ and Windebank AJ (1996) Suramin induces phosphorylation of the high-affinity nerve growth factor receptor in PC12 cells and dorsal root ganglion neurons. J Neurochem 66:963-972.-- therefor.

In the Claims

In claim 2, column 28, line 42, delete "aninline-4-sulfonic acid" and replace with --aniline-4-sulfonic acid-- therefor.

In claim 2, column 28, line 43, delete "aninline-3-phosphonic acid" and replace with --aniline-3-phosphonic acid-- therefor.

In claim 7, column 28, line 55, after the word --of--, delete "from".

Signed and Sealed this
Twenty-first Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,633,250 B2
APPLICATION NO. : 11/622285
DATED : January 21, 2014
INVENTOR(S) : Rick G. Schnellmann et al.

It is certified that error appears in the above-identified patent and that said Letters Patent is hereby corrected as shown below:

On title page, item (54), and in the Specification, Column 1, lines 1-3, delete "CELL REPAIR AND REGENERATION BY SURAMIN AND RELATED POLYSULFONATED NAPTHYLUREAS" and replace with --CELL REPAIR AND REGENERATION BY SURAMIN AND RELATED POLYSULFONATED NAPHTHYLUREAS-- therefor.

On title page, item (56) References Cited - Other Publications, delete the 9th reference on page 1 "Atfi A, Drobetsky E, Boissonneault M, Chapdelaine a and Chevalier S (1994) Transforming growth factor beta down-regulates Src family protein tyrosine kinase signaling pathways. J Biol Chem 269:30688-30693." and replace with --Atfi A, Drobetsky E, Boissonneault M, Chapdelaine A and Chevalier S (1994) Transforming growth factor beta down-regulates Src family protein tyrosine kinase signaling pathways. J Biol Chem 269:30688-30693.-- therefor.

On title page, item (56) References Cited - Other Publications, delete the 17th reference on page 2 "Gill JS Connolly DC, McManus MJ, Maihle NJ and Windebank AJ (1996) Suramin induces phosphorylation of the high-affinity nerve growth factor receptor in PC12 cells and dorsal root ganglion neurons. J Neurochem 66:963-972." and replace with --Gill JS, Connolly DC, McManus MJ, Maihle NJ and Windebank AJ (1996) Suramin induces phosphorylation of the high-affinity nerve growth factor receptor in PC12 cells and dorsal root ganglion neurons. J Neurochem 66:963-972.-- therefor.

In the Claims

In claim 2, column 28, line 42, delete "aninline-4-sulfonic acid" and replace with --aniline-4-sulfonic acid-- therefor.

This certificate supersedes the Certificate of Correction issued October 21, 2014.

Signed and Sealed this
Eleventh Day of November, 2014

Michelle K. Lee
*Deputy Director of the United States Patent and Trademark Office*

CERTIFICATE OF CORRECTION (continued)
U.S. Pat. No. 8,633,250 B2

In claim 2, column 28, line 43, delete "aninline-3-phosphonic acid" and replace with --aniline-3-phosphonic acid-- therefor.

In claim 7, column 28, line 55, after the word --of--, delete "from".

UNITED STATES PATENT AND TRADEMARK OFFICE
CERTIFICATE OF CORRECTION

| | | |
|---|---|---|
| PATENT NO. | : 8,633,250 B2 | Page 1 of 1 |
| APPLICATION NO. | : 11/622285 | |
| DATED | : January 21, 2014 | |
| INVENTOR(S) | : Schnellmann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 456 days.

Signed and Sealed this
Twenty-first Day of April, 2015

Michelle K. Lee
*Director of the United States Patent and Trademark Office*